US008507205B2

(12) United States Patent
Faham et al.

(10) Patent No.: US 8,507,205 B2
(45) Date of Patent: Aug. 13, 2013

(54) SINGLE CELL ANALYSIS BY POLYMERASE CYCLING ASSEMBLY

(75) Inventors: Malek Faham, Pacifica, CA (US);
Thomas Willis, San Francisco, CA (US)

(73) Assignee: Sequenta, Inc., San Francisco, CA (US)

( * ) Notice: Subject to any disclaimer, the term of this patent is extended or adjusted under 35 U.S.C. 154(b) by 0 days.

(21) Appl. No.: 13/100,395

(22) Filed: May 4, 2011

(65) Prior Publication Data

US 2011/0207617 A1    Aug. 25, 2011

Related U.S. Application Data

(63) Continuation-in-part of application No. 12/615,263, filed on Nov. 9, 2009, now Pat. No. 8,236,503.

(60) Provisional application No. 61/112,693, filed on Nov. 7, 2008, provisional application No. 61/332,175, filed on May 6, 2010, provisional application No. 61/446,822, filed on Feb. 25, 2011, provisional application No. 61/452,594, filed on Mar. 14, 2011.

(51) Int. Cl.
*C12Q 1/68* (2006.01)
*C12P 19/34* (2006.01)

(52) U.S. Cl.
USPC ........................................ 435/6.12; 435/91.2

(58) Field of Classification Search
USPC ................................. 435/6.12, 91.2
See application file for complete search history.

(56) References Cited

U.S. PATENT DOCUMENTS

| 5,296,351 | A | 3/1994 | Morley |
| 5,298,396 | A | 3/1994 | Kotzin et al. |
| 5,336,598 | A | 8/1994 | Kotzin et al. |
| 5,418,134 | A | 5/1995 | Morley |
| 5,635,354 | A | 6/1997 | Kourilsky et al. |
| 5,698,396 | A | 12/1997 | Pfreundschuh |
| 5,776,708 | A | 7/1998 | Kotzin et al. |
| 5,837,447 | A | 11/1998 | Gorski ............................ 435/6 |
| 6,087,096 | A | 7/2000 | Dau et al. |
| 6,258,568 | B1 | 7/2001 | Nyren |
| 6,416,948 | B1 | 7/2002 | Pilarski et al. |
| 6,596,492 | B2 | 7/2003 | Avery et al. |
| 6,667,159 | B1 | 12/2003 | Walt .............................. 435/7.32 |
| 6,964,850 | B2 | 11/2005 | Bevilacqua |
| 7,306,906 | B2 | 12/2007 | Maruyama et al. |
| 7,375,211 | B2 | 5/2008 | Kou ............................ 536/24.33 |
| 7,691,994 | B2 | 4/2010 | Brewer ....................... 536/24.33 |
| 7,749,697 | B2 | 7/2010 | Oleksiewicz ...................... 435/6 |
| 8,283,294 | B2 | 10/2012 | Kastrup ........................... 506/17 |
| 2002/0076725 | A1 | 6/2002 | Toyosaki-Maeda et al. |
| 2003/0162197 | A1 | 8/2003 | Morley et al. |
| 2004/0248172 | A1 | 12/2004 | Samoszuk et al. |
| 2005/0064421 | A1 | 3/2005 | Gehrmann ....................... 435/6 |
| 2006/0046258 | A1 | 3/2006 | Lapidus et al. |
| 2006/0085139 | A1 | 4/2006 | Collette et al. |
| 2006/0088876 | A1 | 4/2006 | Bauer |
| 2006/0134125 | A1 | 6/2006 | Luxembourg et al. |
| 2006/0147925 | A1 | 7/2006 | Morley et al. |
| 2006/0234234 | A1 | 10/2006 | Van Dongen ..................... 435/6 |
| 2006/0259248 | A1 | 11/2006 | Collette et al. |
| 2007/0105105 | A1 | 5/2007 | Clelland et al. |
| 2007/0117134 | A1 | 5/2007 | Kou ............................ 536/24.33 |
| 2007/0161001 | A1 | 7/2007 | Leshkowitz ...................... 435/6 |
| 2007/0238099 | A1 | 10/2007 | Cohen et al. |
| 2007/0286849 | A1 | 12/2007 | Chaturvedi |
| 2008/0108509 | A1 | 5/2008 | Haupl et al. |
| 2008/0166704 | A1 | 7/2008 | Marche et al. |
| 2008/0166718 | A1 | 7/2008 | Lim et al. |
| 2008/0248484 | A1 | 10/2008 | Bauer |
| 2008/0280774 | A1 | 11/2008 | Bureznski |
| 2008/0286777 | A1 | 11/2008 | Candeias ........................... 435/6 |
| 2009/0053184 | A1 | 2/2009 | Morgan et al. |
| 2009/0098555 | A1 | 4/2009 | Roth et al. |
| 2009/0181859 | A1 | 7/2009 | Muraguchi ...................... 506/10 |
| 2009/0197257 | A1 | 8/2009 | Harris |
| 2009/0226975 | A1 | 9/2009 | Sabot et al. |
| 2009/0280489 | A1 | 11/2009 | Devinder et al. |
| 2009/0298060 | A1 | 12/2009 | Lal et al. |
| 2010/0021896 | A1 | 1/2010 | Han ................................. 435/6 |
| 2010/0021984 | A1 | 1/2010 | Edd ............................... 435/174 |
| 2010/0035764 | A1 | 2/2010 | Chen ................................. 506/9 |
| 2010/0040606 | A1 | 2/2010 | Lantto et al. |
| 2010/0042329 | A1 | 2/2010 | Hood et al. |
| 2010/0151471 | A1 | 6/2010 | Faham et al. |
| 2010/0173394 | A1 | 7/2010 | Colston, Jr. ................. 435/287.2 |
| 2010/0255471 | A1 | 10/2010 | Clarke .............................. 435/6 |
| 2010/0285975 | A1 | 11/2010 | Mathies ........................... 506/7 |
| 2010/0330571 | A1 | 12/2010 | Robins ............................. 435/6 |
| 2011/0003291 | A1 | 1/2011 | Pasqual ............................ 435/6 |
| 2011/0207134 | A1 | 8/2011 | Faham et al. |
| 2011/0207135 | A1 | 8/2011 | Faham et al. |
| 2012/0220466 | A1 | 8/2012 | Fire et al. |

FOREIGN PATENT DOCUMENTS

| EP | 1544308 | A1 | 6/2005 |
| EP | 1549764 | B1 | 7/2005 |

(Continued)

OTHER PUBLICATIONS

U.S. Appl. No. 13/174,086, filed Jun. 30, 2011, Faham et al.
U.S. Appl. No. 13/196,885, filed Aug. 2, 2011, Faham et al.
U.S. Appl. No. 61/045,586, filed Apr. 16, 2008, Han et al.
Cronn, et al. Multiplex sequencing of plant chloroplast genomes using Solexa sequencing-by-synthesis technology. Nucleic Acids Res. Nov. 2008;36(19):e122.
Curran et al., "Nucleotide sequencing of psoriatic arthritis tissue before and during methotrexate administration reveals a complex inflammatory T cell infiltrate with very few clones exhibiting features that suggest they drive the inflammatory process by recognizing autoantigens," J Immunol 172:1935-1944 (2004).

(Continued)

*Primary Examiner* — Kenneth R. Horlick
*Assistant Examiner* — Joyce Tung
(74) *Attorney, Agent, or Firm* — Wilson Sonsini Goodrich & Rosati

(57) ABSTRACT

The invention provides a method of making measurements on individual cells of a population, particularly cells that have identifying nucleic acid sequences, such as lymphoid cells. In one aspect, the invention provides a method of making multiparameter measurements on individual cells of such a population by carrying out a polymerase cycling assembly (PCA) reaction to link their identifying nucleic acid sequences to other cellular nucleic acids of interest. The fusion products of such PCA reaction are then sequenced and tabulated to generate multiparameter data for cells of the population.

6 Claims, 8 Drawing Sheets

(56) References Cited

FOREIGN PATENT DOCUMENTS

| | | |
|---|---|---|
| JP | 2007-536939 A | 12/2007 |
| JP | 2008099588 A | 5/2008 |
| WO | WO 93/01838 A1 | 2/1993 |
| WO | WO 2005/059176 A1 | 6/1995 |
| WO | WO 97/18330 A1 | 5/1997 |
| WO | WO 98/01738 A1 | 1/1998 |
| WO | WO 03/044225 A2 | 5/2003 |
| WO | WO 03/059155 A2 | 7/2003 |
| WO | WO 2004/003820 A2 | 1/2004 |
| WO | WO 03/059155 A3 | 3/2004 |
| WO | WO 2004/033728 A2 | 4/2004 |
| WO | WO 2004/034031 A2 | 4/2004 |
| WO | WO 2004/044209 A1 | 5/2004 |
| WO | WO 2004/046098 A2 | 6/2004 |
| WO | WO 2004/063706 A2 | 7/2004 |
| WO | WO 2004/046098 A3 | 8/2004 |
| WO | WO 2004/096985 A2 | 11/2004 |
| WO | WO 2005/005651 A2 | 1/2005 |
| WO | WO 2005/042774 A2 | 5/2005 |
| WO | WO 2005/053603 A2 | 6/2005 |
| WO | WO 2005/084134 A2 | 9/2005 |
| WO | WO 2006/076205 A2 | 7/2006 |
| WO | WO 2006/116155 A2 | 11/2006 |
| WO | WO 2008/026927 A2 | 3/2008 |
| WO | WO 2008/026927 A3 | 4/2008 |
| WO | WO 2008/039694 A2 | 4/2008 |
| WO | WO 2008/108803 A2 | 9/2008 |
| WO | WO 2008/108803 A3 | 12/2008 |
| WO | WO 2008/147879 A1 | 12/2008 |
| WO | WO2009/015296 | 1/2009 |
| WO | WO 2009/019657 A2 | 2/2009 |
| WO | WO2009/021215 | 2/2009 |
| WO | WO 2006/076205 A3 | 4/2009 |
| WO | WO 2009/045898 A2 | 4/2009 |
| WO | WO 2009/070767 A2 | 6/2009 |
| WO | WO 2009/019657 A3 | 8/2009 |
| WO | WO 2009/108860 A2 | 9/2009 |
| WO | WO 2009/108866 A2 | 9/2009 |
| WO | WO 2009/070767 A3 | 10/2009 |
| WO | WO 2009/108866 A3 | 10/2009 |
| WO | WO 2009/137255 A2 | 11/2009 |
| WO | WO 2009/137832 A2 | 11/2009 |
| WO | WO2009/145925 | 12/2009 |
| WO | WO 2009/151628 A2 | 12/2009 |
| WO | WO 2009/158521 A2 | 12/2009 |
| WO | WO 2009/108860 A3 | 1/2010 |
| WO | WO 2009/137255 A3 | 1/2010 |
| WO | WO 2010/011894 A1 | 1/2010 |
| WO | WO 2009/151628 A3 | 2/2010 |
| WO | WO2010/0363352 | 4/2010 |
| WO | WO 2009/158521 A3 | 5/2010 |
| WO | WO 2010/151416 A1 | 12/2010 |
| WO | WO 2011/083296 A1 | 7/2011 |
| WO | WO 2011/106738 A2 | 9/2011 |
| WO | WO 2011/139372 A1 | 11/2011 |
| WO | WO 2011/140433 A2 | 11/2011 |
| WO | WO 2011/106738 A3 | 12/2011 |
| WO | WO 2012/048340 A2 | 4/2012 |
| WO | WO 2012/048340 A3 | 6/2012 |

OTHER PUBLICATIONS

Deng et al., "Gene profiling involved in immature CD4+ T lymphocyte responsible for systemic lupus erythematosus," Molecular Immunology 43:1497-1507 (2006).

Dohm, et al. Substantial biases in ultra-short read data sets from high throughput DNA sequencing. Nucleic Acids Research. 2008; 36:e105.

Du et al., "TCR spectratyping revealed T lymphocytes associated with graft-versus-host disease after allogeneic hematopoietic stem cell transplantation," Leukemia & Lymphoma 48(8):1618-1627 (2007).

Fritz et al., "Alterations in the spinal cord T cell repertoire during relapsing experimental autoimmune encephalomyelitis," J Immunol 164:6662-6668 (2000).

Garcia-Castello, et al. Detection of clonal immunoglobulin and T-cell receptor gene recombination in hematological malignancies: monitoring minimal residual disease. Cardiovascular & Haematological Disorders-Drug Targets. 2009; 9:124-135.

Gonzalez, et al. Incomplete DJH rearrangements as a novel tumar target for minimal residual disease quantitation in multiple myeloma using real-time PCR. Leukemia. 2003; 17:1051-1057.

Gonzalez, et al. Incomplete DJH rearrangements of the IgH gene are frequent in multiple myelioma patients: immunobioligcal characteristics and clinical applications. Leukemia. 2003; 17:1398-1403.

Han, et al. Immunorepertoire analysis by multiplex PCR amplification and high throughput sequencing. Abstract. The 96 Annual Meeting of the American Association of Immunologists, Seattle, Washington, May 8-12, 2009. Available at http://jimmunol.org//cgi/content/meeting_abstract/182/1_MeetingAbstracts/42.6?sid=25 7929f1-97a9-4330-8e96-1750aa240e69. Accessed Nov. 24, 2010.

Heger, M. Studies Highlight Challenges of Immune Repertoire Sequencing's Clinical Applicability. Available at http://www.genomeweb.com/sequencing/studies-highlight-challenges-immune-repertoire-sequencings-clinical-applicabilit?hq_e=el&hq_m=966798&hq_1=10&hq_v=2357e2f0b3. Accessed Apr. 6, 2011.

Holt, "Q &A: BC cancer agency's Robert Holt on sequencing the immune repertoire in immune reconstitution," Genome Web (www.genomeweb.com) Jun. 30, 2009.

International Search Report for PCT Application PCT/US2009/006053 dated Jun. 15, 2010.

Ishii et al., "Isolation and expression profiling of genes upregulated in the peripheral blood cells of systemic lupus erythematosus patients," DNA Research 12:429-439 (2005).

Jacobi et al., "Activated memory B cell subsets correlate with disease activity in systemic lupus erythematosus: delineation by expression of CD27, IgD, and CD95," Arthritis & Rheumatism 58(6):1762-1773 (2008).

Jacobi et al., "Correlation between circulating CD27high plasma cells and disease activity in patients with systemic lupus erythematosus," Arthritis & Rheumatism 48(5):1332-1342 (2003).

Kato et al., "Analysis of accumulated T cell clonotypes in patients with systemic lupus erythematosus," Arthritis & Rheumatism 43(12):2712-2721 (2000).

Kneba, et al. Analysis of rearranged T-cell receptor beta-chain genes by polymerase chain reaction (PCR0 DNA sequencing and automated high resolution PCR fragment analysis. Blood. 1995; 86:3930-3937.

Laplaud et al., "Blood T-cell receptor β chain transcriptome in multiple sclerosis. Characterization of the T cells with altered CDR3 length distribution," Brain 127:981-995 (2004).

Laplaud et al., "Serial blood T cell repertoire alterations in multiple sclerosis patients; correlation with clinical and MRI parameters," J Neroimmunol 177:151-160 (2006).

Li, et al. Sequence analysisn of clonal immunoglobulin and T-cell receptor gene rearrangements in children with acute lymphoblastic leukemia at diagnosis and at relapse: implications for pathogenesis and for the clinical utility of PCR-based methods of minimal residual disease detection. Blood. 2003; 102:4520-4526.

Luo et al., "Analysis of the interindividual conservation of T cell receptor α- and β-chain variable regions gene in the peripheral blood of patients with systemic lupus erythematosus," Clin Exp Immunol 154:316-324 (2008).

Mato et al., "Correlation of clonal T cell expansion with disease activity in systemic lupus erythematosus," Int Immunol 9(4):547-554 (1997).

Matsumoto et al., "CDR3 spectratyping analysis of the TCR repertoire in myasthenia gravis," J Immunol 176:5100-5107 (2006).

Matsumoto et al., "Complementarity-determining region 3 spectratyping analysis of the TCR repertoire in multiple sclerosis," J Immunol 170:4846-4853 (2003).

Menezes et al., "A public T cell clonotype within a heterogeneous autoreactive repertoire is dominant in driving EAE," J Clin Invest 117(8):2176-2185 (2007).

Michalek, et al. Detection and long-term in vivo monitoring of individual tumor-specific T cell clones in patients with metastatic melanoma. J Immunol. Jun. 1, 2007;178(11):6789-95.

Muraro et al., "Molecular tracking of antigen-specific T cell clones in neurological immune-mediated disorders," Brain 126:20-31 (2003).
Notification of Grant dated Jul. 26, 2011 for patent serial No. GB 2467704.
Ogle, et al. Direst measurement of lymphocyte receptor diversity. Nucleic Acids Research. 2003; 31(22):e139.
Okajima et al., "Analysis of T cell receptor Vβ diversity in peripheral CD4+ and CD8+ T lymphocytes in patients with autoimmune thyroid diseases," Clin Exp Immunol 155:166-172 (2008).
Pop, et al. Bioinformatics challenges of new sequencing technology. Trends Genet. Mar. 2008;24(3):142-9.
Reinartz, et al. Massively parallel signature sequencing (MPSS) as a tool for in-depth quantitative gene expression profiling in all organisms. Brief Funct Genomic Proteomic. Feb. 2002;1(1):95-104.
Risitano et al., "In-vivo dominant immune responses in aplastic anaemia: molecular tracking of putatively pathogenetic T-cell clones by TCR β-CDR3 sequencing," Lancet 364:355-364 (2004).
Schwab et al., "CD8+ T-cell clones dominate brain infiltrates in Rasmussen encephalitis and persist in the periphery," Brain 132:1236-1246 (2009).
Shen, et al. Comparing platforms for C. elegans mutant identification using high-throughput whole-genome sequencing. PLoS One. 2008;3(12):e4012.
Skulina et al., "Multiple sclerosis: brain-infiltrating CD8+ T cells persist as clonal expansions in the cerebrospinal fluid and blood," PNAS 101(8):2428-2433 (2004).
Sumida et al., "T cell receptor repertoire of infiltrating T cells in lips of Sjögren's syndrome patients," J Clin Invest 89:681-685 (1992).
Sumida et al., "T cell receptor Vα repertoire of infiltrating T cells in labial salivary glands from patients with Sjögren's syndrome," J Rheumatol 21: 1655-1661 (1994).
Tackenberg et al., "Clonal expansions of CD4+ β helper T cells in autoimmune myasthenia gravis," Eur J Immunol 37:849-863 (2007).
UK Combined Search Report and Office action dated May 26, 2011 for UK application No. GB1105068.9.
UK Search Report dated Jul. 6, 2010 for UK application No. GB1009641.0.
Umibe et al., "Clonal expansion of T cells infiltrating in the airways of non-atopic asthmatics," Clin Exp Immunol 119:390-397 (2000).
Warren et al., "Profiling model T-cell metagenomes with short reads," Bioinformatics 25(4):458-464 (2009).
Warren, et al. Exhaustive T-cell repertoire sequencing of human peripheral blood samples reveals signatures of antigen selection and a directly measured repertoire size of at least 1 million clonotypes. Genome Res. Feb. 24, 2011. [Epub ahead of print].
Wlodarski, et al. Molecular strategies for detection and quantitation of the clonal cytotoxic T-cell responses in aplastic anemia and myelodysplastic syndrome. Blood. 2006; 108:2632-2641.
Wlodarski, et al. Pathologic clonal cytotoxic T-cell responses: nonrandom nature of the T-cell-receptor restriction in large granular lymphocyte leukemia. Blood. 2005; 106:2769-2779.
Yin et al., "Antiretroviral therapy restores diversity in the T-cell receptor Vβ repertoire of CD4 T-cell subpopulations among human immunodeficiency virus type 1-infected children and adolescents," Clin Vac Immunol 16(9):1293-1301 (2009).
Batzoglou. The many faces of sequence alignment. Briefings in Bioinformatics. 2005; 6:6-22.
Giuggio, et al. Evolution of the intrahepatic T cell repertoire during chronic hepatitis C virus infection. Viral Immunol. 2005;18(1):179-89.
Kobari, et al. T cells accumulating in the inflamed joints of a spontaneous murine model of rheumatoid arthritis become restricted to common clonotypes during disease progression. Int Immunol. Jan. 2004;16(1):131-8.
Rougemont, et al. Probabilistic base calling of Solexa sequencing data. BMC Bioinformatics. 2008; 9:431.
UK Search Report dated May 25, 2011 for UK application No. GB1009641.0.
Arstila et al, "A direct estimate of the human αβ T cell receptor diversity," Science, 286; 958-961 (1999).
Boria et al, "Primer sets for cloning the human repertoire of T cell receptor variable regions," BMC Immunology, 9: 50 (2008).
Boyd et al, "Measurement and clinical monitoring of human lymphocyte clonality by massively parallel VDJ pyrosequencing," Science Transl. Med. 1(12), 12ra23 (2009).
Brehm-Stecher et al, "Single-cell microbiology: tools, technologies, and applications," Microbiology and Molecular Biology Reviews, 68(3): 538-559 (2004).
Campbell et al, "Subclonal phylogenic structures in cancer revealed by ultra-deep sequencing," Proc. Natl. Acad. Sci., 105(35): 13081-13086 (2008).
Davis et al, "Staining of cell surface human CD4 with2'-F-pyrimidine-containing RNA amptamers for flow cytometry," Nucleic Acids Research, 26(17): 3915-3924 (1998).
Edd et al, "Controlled encapsulation of single cells into monodisperse picoliter drops," Lab Chip, 8(8): 1262-1264 (2008).
Freeman et al, "Profiling the T-cell receptor beta-chain repertoire by massively parallel sequencing," Genome Research, 19(10): 1817-1824 (2009).
Jena et al, "Amplification of genes, single transcripts and cDNA libraries from one cell and direct sequence analysis of amplified products derived from one molecule," J, Immunol. Methods, 190: 199-213 (1996).
Kim et al, "An efficient and reliable DNA extraction method for preimplantation genetic diagnosis: a comparison of allele drop out and amplification rates using different single cell lysis methods," Fertility and Sterility, 92: 814-818 (2009).
Li et al, "An improved one-tube RT-PCR protocol for analyzing single-cell gene expression in individual mammalian cells," Anal. Bioanal. Chem., 397: 1853-1859 (2010).
Novak et al, "Single-cell multiplex gene detection and sequencing with microfluidically generated agarose emulsions," Angewandte Chemie, 50: 390-395, with supplemental material (2011).
Packer et al, "Optimized clonotypic analysis of T-cell receptor repertoire in immune reconstitution," Experimental Hematology, 35: 516-521 (2007).
Ray et al, "Single cell multiplex PCR amplification of five dystrophin gene exons combined with gender determination," Molecular Human Reproduction, 7(5): 489-494 (2001).
Robins et al, "Comprehensive assessment of T-cell receptor β chain diversity in αβ T cells," Blood, 114(19): 4099-4107 (2009).
Thornhill et al, "A comparison of different lysis buffers to assess allele dropout from single cells for preimplantation genetic diagnosis," Prenatal Diagnosis, 21: 490-497 (2001).
Tokimitsu et al, "Cell-microarray analysis of antigen-specific B-cells: single cell analysis of antigen receptor expression and specificity," Cytometry Part A, 71A: 961-967 (2007).
Tokimitsu et al, "Single lymphocyte analysis with a microwell array chip." Cytometry Part A, 71A: 1003-1010 (2007).
Wang, et al. High throughput sequencing reveals a complex pattern of dynamic interrelationships among human T cells subsets. Proc Natl Acad Sci USA. Jan. 26, 2010; 107(4): 1518-1523.
Weinstein et al, "High throughput sequencing of the zebrafish antibody repertoire," Science, 324: 807-810 (2009).
Wells et al, "Strategies for preimplantation genetic diagnosis of single gene disorders by DNA amplification," Prenatal Diagnosis, 18: 1389-1401 (1998).
Wetmur et al, "An emulsion polymerase chain reaction-based method molecular haplotyping," Methods in Molecular Biology, 410: 351-361 (1996).
Wetmur et al, "Molecular haplotyping by linking emulsion PCR: analysis of paraoxonase 1 haplotypes and phenotypes," Nucleic Acids Research, 33(8) 2615-2619 (2005).
Wetmur et al, "Linking emulsion PCR haplotype analysis," chapter 11, in Park (editor), PCR Protocols, Methods in Molecular Biology, 687: 165-175 (2011).
Yon et al, "Precise gene fusion by PCR," Nucleic Acids Research, 17(12):4895 (1989).
Zeng et al, "High-performance single cell genetic analysis using microfluidic emulsion generator arrays," Anal. Chem., 82: 3183-3190 (2010).
Zhou et al, "High throughput analysis of TCR-β rearrangement and gene expression in single cells," Laboratory Investigation, 86: 314-321 (2006).
U.S. Appl. No. 13/214,111, filed Aug. 19, 2011, Faham et al.

U.S. Appl. No. 13/369,031, filed Feb. 8, 2012, Faham et al.
Choi, et al. Clonal evolution in B-lineage acute lymphoblastic leukemia by contemporaneous VH-VH gene replacements and VH-DJH gene rearrangements. Blood. Mar. 15, 1996;87(6):2506-12.
Costabile, et al. Molecular approaches in the diagnosis of primary immunodeficiency diseases. Hum Mutat. Dec. 2006;27(12):1163-73.
International search report and written opinion dated Sep. 22, 2011 for PCT Application No. US11/000791.
International search report and written opinion dated Oct. 19, 2011 for PCT Application No. US11/000792.
Kim, et al. Polony multiplex analysis of gene expression (PMAGE) in mouse hypertrophic cardiomyopathy. Science. Jun. 8, 2007;316(5830):1481-4.
Margulies, et al. Genome sequencing in microfabricated high-density picolitre reactors. Nature. Sep. 15, 2005;437(7057):376-80. Epub Jul. 31, 2005.
Nardi, et al. Quantitative monitoring by polymerase colony assay of known mutations resistant to ABL kinase inhibitors. Oncogene. Jan. 31, 2008;27(6):775-82. Epub Aug. 6, 2007, 1-8.
UK office action dated May 25, 2011 for UK application No. GB1009641.0.
UK office action dated Oct. 20, 2010 for UK application No. GB1009641.0.
UK Search Report and office action dated Jan. 12, 2012 for UK application No. GB1120209.0.
UK Search Report and office action dated Jul. 7, 2010 for UK application No. GB1009641.0.
Van Dongen, et al. Design and standardization of PCR primers and protocols for detection of clonal immunoglobulin and T-cell receptor gene recombinations in suspect lymphoproliferations: report of the BIOMED-2 Concerted Action BMH4-CT98-3936. Leukemia. Dec. 2003;17(12):2257-317.
U.S. Appl. No. 12/945,678, filed Nov. 12, 2010, Faham et al.
U.S. Appl. No. 13/627,497, filed Sep. 26, 2012, Faham et al.
Dou, et al. Analysis of T cell receptor Vbeta gene usage during the course of disease in patients with chronic hepatits B. J Biomed Sci. Nov.-Dec. 1998;5(6):428-34.
Pira, et al. Human navie CD4 T-cell clones specific for HIV envelope persist for years in vivo in the absence of antigenic. J Acquir Immune Defic Syndr. Oct. 1, 2005;40(2):132-9.
Ria, et al. Collagen-Specific T-cell repertoire in blood and synovial fluid varies with disease activity in early rheumatoid arthritis. Arthritis Res Ther. 2008;10(6):R135. Epub Nov. 17, 2008.
Rickinson, et al. Human cytotoxic T lymphocyte responses to Epstein-Barr virus infection. Annu Rev Immunol. 1997;15:405-31.
Schaufelberger, et al. An uneven expression of T cell receptor V genes in the arterial wall and peripheral blood in giant cell arteritis. Inflammation. Dec. 2008;31(6):372-83.
Scholler, et al. Analysis of T cell receptor alpha beta veriability in lymphocytes infiltrating melanoma primary tumours and metastatic lesions. Cancer Immunol Immunother. Oct. 1994;39(4):239-48.
Struyk, et al. T cell receptors in rheumatoid arthritis. Arthritis Rheum. May 1995;38(5):577-89.
U.S. Appl. No. 13/459,701, filed Apr. 30, 2012, Faham et al.
U.S. Appl. No. 13/468,323, filed May 10, 2012, Faham et al.
U.S. Appl. No. 13/487,980, filed Jun. 4, 2012, Faham et al.
Bene, et al. How and why minimal residual disease studies are necessary in leukemia; a review from WP10 and WP12 of the European LeukaemiaNet. Haematologica. Aug. 2009;94(8):1135-50. Epub Jul. 7, 2009.
Benichou, et al. Rep-Seq: uncovering the immunological repertoire through next-generation sequencing. Immunology. Mar. 2012;135(3):183-91. doi: 10.1111/j.1365-2567.2011.03527.x.
Bonarius, et al. Monitoring the T-Cell Receptor Repertoire at Single-Clone Resolution. PLoS One. Dec. 20, 2006;1:e55.
Boyd, et al. Individual variation in the germline Ig gene repertoire inferred from variable region gene rearrangements. J Immunol. Jun. 15, 2010;184(12):6986-92. Epub May 21, 2010.
Brisco, et al. Determining the repertoire of IGH gene rearrangements to develop molecular markers for minimal residual disease in B-lineage acute lymphoblastic leukemia. J Mol Diagn. May 2009;11(3):194-200. Epub Mar. 26, 2009.

Bruggemann, et al. Clinical significance of minimal residual disease quantification in adult patients with standard-risk acute lymphoblastic leukemia. Blood. Feb. 1, 2006;107(3):1116-23. Epub Sep. 29, 2005.
Campana. Minimal residual disease in actue lymphoblastic leukemia. Semin Hematol. Jan. 2009;46(1):100-6.
Choi, et al. Relapse in children with acute lymphoblastic leukemia involving selection of a preexisting drug-resistant subclone. Blood. Jul. 15, 2007;110(2):632-9. Epub Mar. 19, 2007.
Currier, et al. Spectratype/immunoscope analysis of the expressed TCR repertoire. Current Protocols in Immunology. 2000; Supplement 38:10.28.1-10.28.24.
European office action dated Mar. 28, 2012 for EP Application No. 09764927.1.
Gorski, et al. Circulating T cell repertoire complexity in normal individuals and bone marrow recipients analyzed by CDR3 size spectratyping. Correlation with immune status. J Immunol. May 15, 1994;152(10):5109-19.
Illumina. Data Sheet: Sequencing. Genomic Sequencing. Pub. No. 770.2008-016 Copyright 2010. Reference states: "Current as of Jan. 30, 2009."
Langerak, et al. Polymerase chain reaction-based clonality testing in tissue samples with reactive lymphoproliferations: usefulness and pitfalls. A report of the BIOMED-2 Concerted Action BMH4-CT98-3936. Leukemia. Feb. 2007;21(2):222-9. Epub Dec. 14, 2006.
Li, et al. Utilization of Ig heavy chain variable, diversity, and joining gene segments in children with B-lineage acute lymphoblastic leukemia: implications for the mechanisms of VDJ recombination and for pathogenesis. Blood. Jun. 15, 2004;103(12):4602-9. Epub Mar. 9, 2004.
Logan, et al. High-throughput VDJ sequencing for quantification of minimal residual disease in chronic lymphocytic leukemia and immune reconstitution assessment. Proc Natl Acad Sci U S A. Dec. 27, 2011;108(52):21194-9. Epub Dec. 12, 2011.
Lovisa, et al. IGH and IGK gene rearrangements as PCR targets for pediatric Burkitt's lymphoma and mature B-ALL MRD analysis. Lab Invest. Oct. 2009;89(10):1182-6.
Meleshko, et al. Rearrangements of IgH, TCRD and TCRG genes as clonality marker of childhood acute lymphoblastic leukemia. Exp Oncol. Dec. 2005;27(4):319-24.
Moss, et al. The human T cell reeptor in health and disease. Annu. Rev. Immunol. 1992; 10:71-96.
Neale, et al. Comparative analysis of flow cytometry and polymerase chain reaction for the detection of minimal residual in childhood acute lymphoblastic leukemia. Leukemia. May 2004;18(5):934-8.
Nguyen, et al. Identification of errors introduced during high throughput sequencing of the T cell receptor repertoire. BMC Genomics. Feb. 11, 2011;12:106.
Office action dated Sep. 15, 2011 for U.S. Appl. No. 12/615,263.
Panzer-Grumayer, et al. Immunogenotype changes prevail in relapses of young children with TEL-AML1-positive acute lymphoblastic leukemia and derive mainly from clonal selection. Clin Cancer Res. Nov. 1, 2005;11(21):7720-7.
Reddy, et al. Systems analysis of adaptive immunity by utilization of high-throughput technologies. Curr Opin Biotechnol. Aug. 2011;22(4):584-9. Epub May 12, 2011.
Robins, et al. Ultra-sensitive detection of rare T cell clones. Immunol Methods. Jan. 31, 2012;375(1-2);14-9. Epub Sep. 10, 2011.
Sramkova, et al. Detectable minimal residual disease before allogeneic hematopoietic stem cell transplantation predicts extremely poor prognosis in children with acute lymphoblastic leukemia. Pediatr Blood Cancer. Jan. 2007;48(1):93-100.
UK Combined Search Report and Office action dated Jun. 29, 2012 for UK application No. GB1209668.1.
Wang, et al. Quantitative measurement of pathogen-specific human memory T cell repertoire diversity using a CDR3 beta-specific microarray. BMC Genomics. Sep. 19, 2007;8:329.
Zaliova, et al. Quantification of fusion transcript reveals a subgroup with distinct biological properties and predicts relapse in BCR/ABL-positive ALL: implications for residual disease monitoring. Leukemia. May 2009;23(5):944-51. Epub Jan. 22, 2009.

Bagnara, et al. IgV gene intraclonal diversification and clonal evolution in B-cell chronic lymphocytic leukaemia. Br J Haematol. Apr. 2006;133(1):50-8.

Beishuizen, et al. Analysis of Ig and T-cell receptor genes in 40 childhood acute lymphoblastic leukemias at diagnosis and subsequent relapse: implications for the detection of minimal residual disease by polymerase chain reaction analysis. Blood. Apr. 15, 1994;83(8):2238-47.

Davi, et al. Lymphocytic progenitor cell origin and clonal evolution of human B-lineage acute lymphoblastic leukemia. Blood. Jul. 15, 1996;88(2):609-21.

Germano, et al. Clonality profile in relapsed precursor-B-ALL children by GeneScan and sequencing analyses. Consequences on minimal residual disease monitoring. Leukemia. Aug. 2003;17(8):1573-82.

Golembowski, et al. Clonal evolution in a primary cutaneous follicle center B cell lymphoma revealed by single cell analysis in sequential biopsies. Immunobiology. Apr. 2000;201(5):631-44.

Green, et al. Clonal diversity of Ig and T-cell-receptor gene rearrangements identifies a subset of childhood B-precursor acute lymphoblastic leukemia with increased risk of relapse. Blood. Aug. 1, 1998;92(3):952-8.

Gurrieri, et al. Chronic lymphocytic leukemia B cells can undergo somatic hypermutation and intraclonal immunoglobulin V(H)DJ(H) gene diversification. J Exp Med. Sep. 2, 2002;196(5):629-39.

Langerak, et al. Immunoglobulin/T-cell receptor clonality diagnostics. Exoert Opin. Med. Diagn. 2007; 1(3):451-461.

Li, et al. Clonal rearrangements in childhood and adult precursor B acute lymphoblastic leukemia: a comparative polymerase chain reaction study using multiple sets of primers. Eur J Haematol. Oct. 1999;63(4):211-8.

Li, et al. Detailed clonality analysis of relapsing precursor B acute lymphoblastic leukemia: implications for minimal residual disease detection. Leukemia Research. 2001; 25:1033-1045.

Matolcsy, et al. Clonal evolution of B cells in transformation from low-to high-grade lymphoma. Eur J Immunol. Apr. 1999;29(4):1253-64.

Pels, et al. Clonal evolution as pathogenetic machanism in relapse of primary CNS lymphoma. Neurology. Jul. 13, 2004;63(1):167-9.

Rosenquist, et al. Clonal evolution as judged by immunoglobulin heavy chain gene rearrangements in relapsing precursor-B acute lymphoblastic leukemia. Eur J Haematol. Sep. 1999;63(3):171-9.

Ryan, et al. Clonal evolution of lympoblastoid cell lines. Lab Invest. Nov. 2006;86(11):1193-200. Epub Oct. 2, 2006.

Steenbergen, et al. Distinct ongoing Ig heavy chain rearrangement processes in childhood B-precursor acute lymphoblastic leukemia. Blood. Jul. 15, 1993;82(2):581-9.

Steward, et al. A polymerase chain reaction study of the stability of Ig heavy-chain and T-cell receptor delta gene rearrangements between presentation and relapse of childhood B-lineage acute lymphoblastic leukemia. Blood. Mar. 1, 1994;83(5):1355-62.

Scheme 1(a)

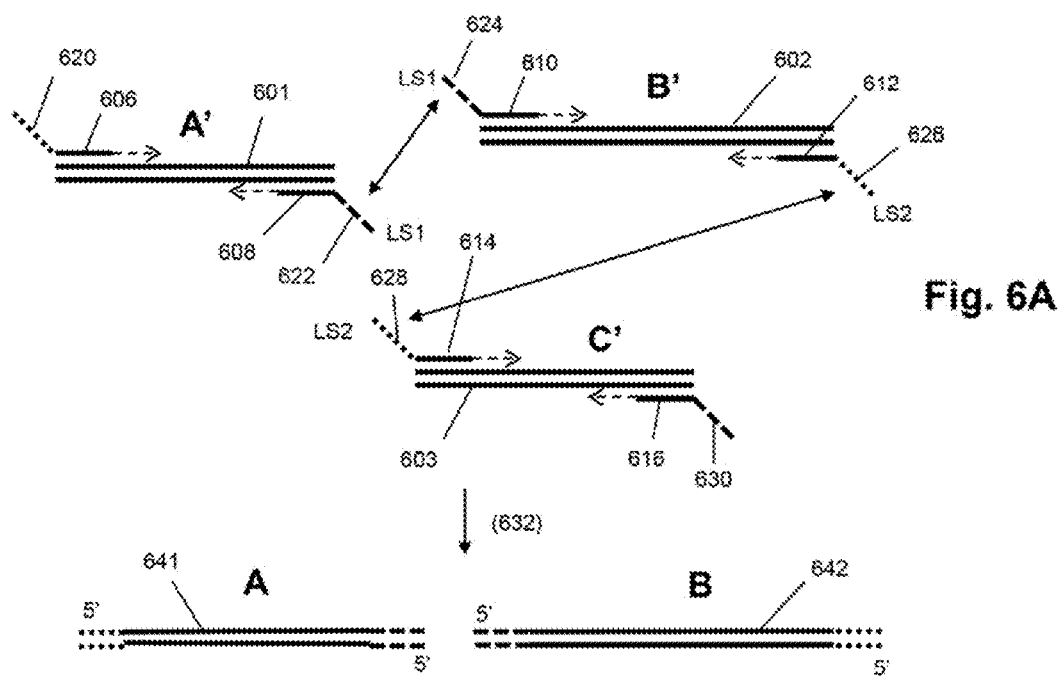
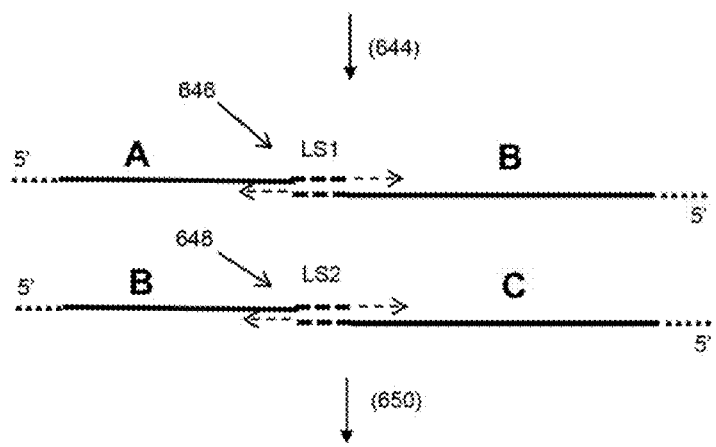
Fig. 6A
Fig. 6B
Fig. 6C

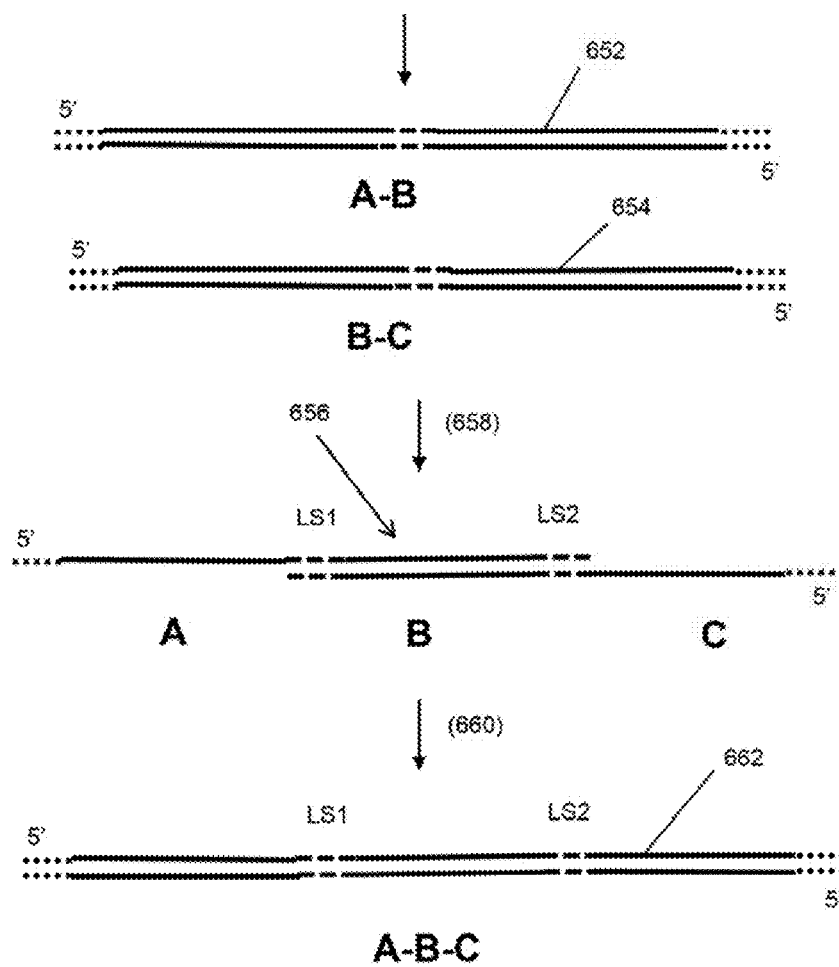

SINGLE CELL ANALYSIS BY POLYMERASE CYCLING ASSEMBLY

This application is a continuation-in-part of U.S. application Ser. No. 12/615,263 filed 9 Nov. 2009, now U.S. Pat. No. 8,236,503, which claims the benefit of U.S. provisional application Ser. No. 61/112,693 filed Nov. 7, 2008; this application also claims priority from U.S. provisional applications Ser. No. 61/332,175 filed 6 May 2010, Ser. No. 61/446,822 filed 25 Feb. 2011, and Ser. No. 61/452,594 filed 14 Mar. 2011, all of which are incorporated herein by reference in their entireties.

BACKGROUND

Cytometry plays an indispensable role in many medical and research fields. Image-based and flow cytometers have found widespread use in these fields for counting cells and measuring their physical and molecular characteristics, e.g. Shapiro, Practical Flow Cytometry, 4th Edition (Wiley-Liss, 2003). In particular, flow cytometry is a powerful technique for rapidly measuring multiple parameters on large numbers of individual cells of a population enabling acquisition of statistically reliable information about the population and its subpopulations. The technique has been important in the detection and management of a range of diseases, particularly blood-related diseases, such as hematopoietic cancers, HIV, and the like, e.g. Woijciech, Flow Cytometry in Neoplastic Hematology, Second Edition (Informa Healthcare, 2010); Brown et al, Clinical Chemistry, 46: 8(B); 1221-1229 (2000). Despite this utility, flow cytometry has a number of drawbacks, including limited sensitivity in rare cell detection, e.g. Campana et al, Hematol. Oncol. Clin. North Am., 23(5): 1083-1098 (2009); limitations in the number of cell parameters that can be practically measured at the same time; and costly instrumentation.

In view of the above, it would be advantageous to many medical and research fields if there were available alternative methods and systems for making multiparameter measurements on large numbers of individual cells that overcame the drawbacks of current cytometric approaches.

SUMMARY OF THE INVENTION

The present invention is directed to methods for making multiparameter measurements of target nucleic acids in single cells of a population, particularly cells such as lymphocytes that contain cell-specific recombined sequences. Aspects of the present invention are exemplified in a number of implementations and applications, some of which are summarized below and throughout the specification.

In one aspect the invention includes a method of analyzing a plurality target nucleic acids in each cell of a population comprising the steps of: (a) providing multiple reactors each containing a single cell in a polymerase cycling assembly (PCA) reaction mixture comprising a pair of outer primers and one or more pairs of linking primers specific for the plurality of target nucleic acids; (b) performing a PCA reaction in the reactors to form fusion products of the target nucleic acids in the reactors; and (c) sequencing the fusion products from the reactors to identify the target nucleic acids of each cell in the population.

In another aspect the invention includes a method of distinguishing multiple subpopulations of lymphocytes comprising the steps of: (a) providing multiple reactors each containing a single lymphocyte in a polymerase cycling assembly (PCA) reaction mixture comprising a pair of outer primers and one or more pairs of linking primers, one or more pairs of such primers being specific for one or more target nucleic acids and at least one pair of such primers being specific for a nucleic acid containing a clonotype; (b) performing a PCA reaction in each reactor to form a fusion product comprising the target nucleic acids and a clonotype of the lymphocyte therein; (c) sequencing the fusion products from the reactors; and (d) classifying each lymphocyte into a subpopulation by the target nucleic acids associated with its clonotype.

These above-characterized aspects, as well as other aspects, of the present invention are exemplified in a number of illustrated implementations and applications, some of which are shown in the figures and characterized in the claims section that follows. However, the above summary is not intended to describe each illustrated embodiment or every implementation of the present invention.

BRIEF DESCRIPTIONS OF THE DRAWINGS

FIGS. 6A-6E illustrate a method of using PCA to link together three sequences.

DETAILED DESCRIPTION OF THE INVENTION

The practice of the present invention may employ, unless otherwise indicated, conventional techniques and descriptions of organic chemistry, molecular biology (including recombinant techniques), cell biology, and biochemistry, which are within the skill of the art. Such conventional techniques include, but are not limited to, sampling and analysis of blood cells, nucleic acid sequencing and analysis, and the like. Specific illustrations of suitable techniques can be had by reference to the example herein below. However, other equivalent conventional procedures can, of course, also be used. Such conventional techniques and descriptions can be found in standard laboratory manuals such as *Genome Analysis: A Laboratory Manual Series* (Vols. I-IV); *PCR Primer: A Laboratory Manual;* and *Molecular Cloning: A Laboratory Manual* (all from Cold Spring Harbor Laboratory Press); and the like.

Figure 1:
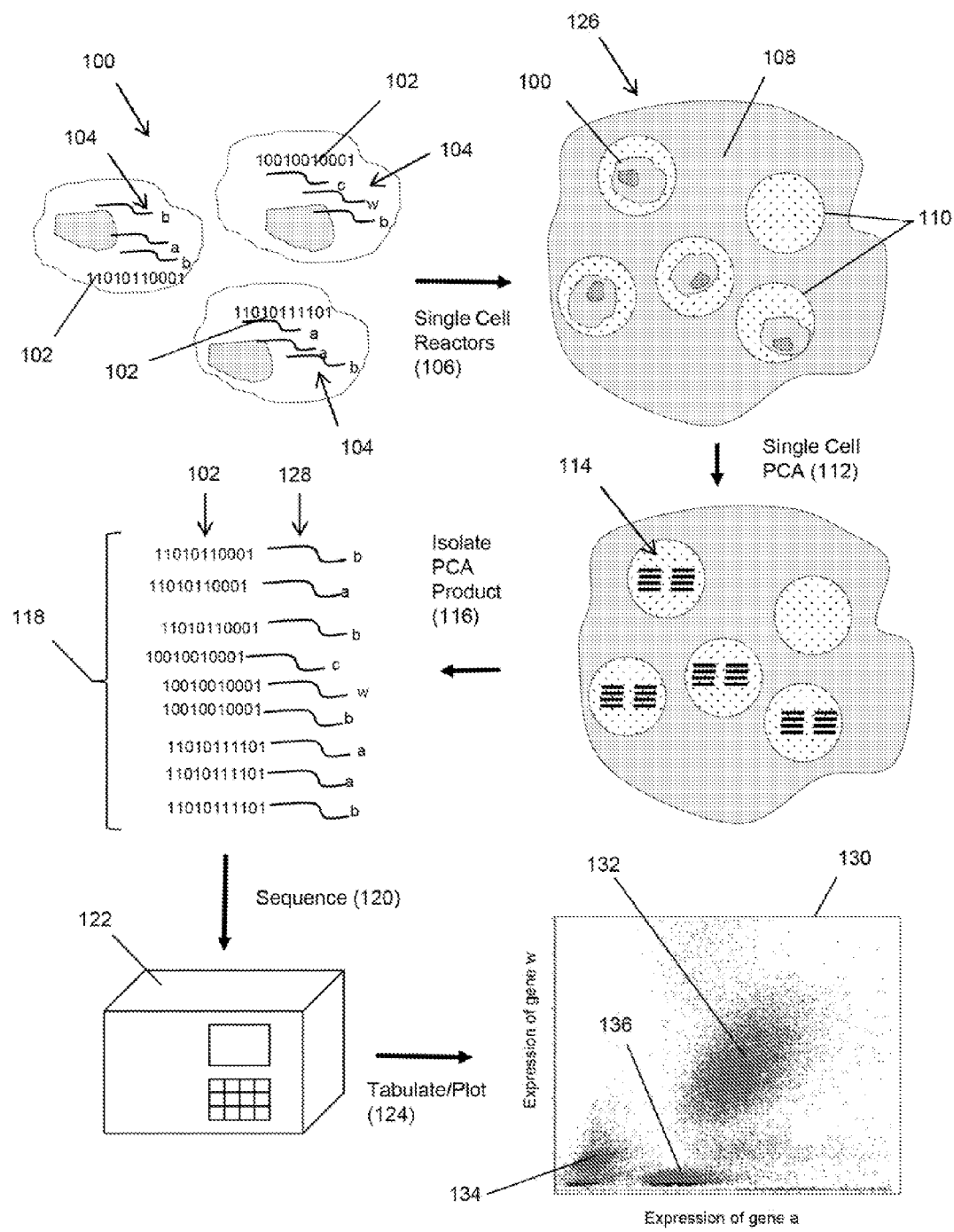
FIG. 1 illustrates steps of one embodiment of the method of the invention.

The invention provides a method of making measurements on individual cells of a population, particularly cells that have identifying nucleic acid sequences, such as lymphoid cells. In one aspect the invention provides a method of making multiparameter measurements on individual cells of such a population. An objective of assays of the invention is to carry out a polymerase cycling assembly (PCA) reaction on individual cells to link their identifying nucleic acid sequences to other cellular nucleic acids of interest (referred to herein as "target nucleic acids"), the products of such linking being referred to herein as "fusion products." After their generation, fusion products can be sequenced and tabulated to generate data, especially multiparameter data, for each cell of a population. In one aspect, such data may include gene expression data, data on the presence or absence of one or more predetermined genomic sequences, gene copy number data, or combinations of the foregoing. FIG. 1 gives an overview on one embodiment of the invention. Lymphoid cells (100) each have a distinct identifying nucleic acid (102), which in the figure is represented as a unique binary number. In one aspect, the identifying nucleic acids are the clonotypes of the lymphocytes. In addition, each cell has and/or expresses various nucleic acids of interest (104), or target nucleic acids, represented by the letters "a", "b", "c" and "w", which may be genomic DNA, expressed genes, or the like. Cells (100) are disposed (106) in single cell reactors (110), which in this example are illustrated as micelles of a water-in-oil emulsion (108), although a variety of single cell reactors may be used, including but not limited to, plates with arrays of nanoliter-volume wells, microfluidic devices, and the like, as described more fully below. In one aspect, single-cell emulsion (126) is generated using a microfluidic emulsion generator, such as disclosed by Zeng et al, Anal. Chem., 82: 3183-3190 (2010), or the like.

Reactors (110) contain a PCA reaction mixture that, for example, may comprise a nucleic acid polymerase, outer primers and linking primers (described more fully below), nucleoside triphosphates, a buffer solution, and the like. In some embodiments, a PCA reaction mixture may also include one or more cell lysing reagents, to access of such reagents to target nucleic acids. For each reactor (110) containing a cell, PCA reaction (112) generates fusion products (114) that may comprise one or more pairs of sequences, such that one member of the pair is the identifying nucleic acid of the cell in the reactor and the other member is a nucleic acid of interest, such as an expressed gene. In other embodiments, fusion products may comprise triplets of sequences, or higher order concatenations. In the method of the invention, a single kind of fusion product may be generated for each cell (or per reactor) or a plurality of different kinds of fusion products may be generated for each cell (or per reactor). Such plurality may be in the range of from 2 to 500, or from 2 to 200, or from 2 to 100, or from 2 to 20. In one embodiment, such plurality may be in the range of from 2 to 10.

After completion of PCA reaction (112), emulsion (126) is broken and fusion products (114) are isolated (116). Fusion products (114) are represented in FIG. 1 as conjugates (118) of identifying nucleic acids (102) and target nucleic acids (128). A variety of conventional methods may be used to isolate fusion products (114), including, but not limited to, column chromatography, ethanol precipitation, affinity purification after use of biotinylated primers, gel electrophoresis, or the like. As part of PCA reaction (112) or after isolation (116), additional sequences may be added to fusion products (114) as necessary for sequencing (120). Sequencing may be carried out using a conventional high-throughput instrument (122), e.g. Genome Analyzer IIx (Illumina, Inc., San Diego), or the like. Data from instrument (122) may be organized and displayed (124) in a variety of ways. In particular, where target nucleic acids are selected gene expression products, e.g. mRNAs, plots may be constructed that display per-cell expression levels of selected gene for an entire population or subpopulation, in a manner similar to that for flow cytometry data, as illustrated by plot (130). Each cell is associated with a unique clonotype that is linked via the PCA reaction to genes expressed in the cell in a proportion related to their cellular abundance. Thus, by counting the number of expressed gene sequences linked to a specific clonotype sequence, one obtains a measure of expression for such gene in the cell associated with the specific clonotype. As illustrated in plot (130), three subpopulations of cells are indicated by the presence of separate clusters (132, 134, and 136) based on expression levels of gene w and gene a. In one aspect, whenever gene expression levels are monitored, at least one gene is selected as an internal standard for normalizing the expression measurements of other genes.

Polymerase Cycling Assembly (PCA) Reaction Formats

Polymerase cycling assembly (PCA) reactions permit a plurality of nucleic acid fragments to be fused together to form a single fusion product in one or more cycles of fragment annealing and polymerase extension, e.g. Xiong et al, FEBS Micro biol. Rev., 32: 522-540 (2008). PCA reactions come in many formats. In one format of interest, PCA follows a plurality of polymerase chain reactions (PCRs) taking place in a common reaction volume, wherein each component PCR includes at least one linking primer that permits strands from the resulting amplicon to anneal to strands from another amplicon in the reaction and to be extended to form a fusion product or a precursor of a fusion product. PCA in its various formats (and under various alternative names) is a well-known method for fragment assembly and gene synthesis, several forms of which are disclosed in the following references: Yon et al, Nucleic Acids Research, 17: 4895 (1989); Chen et al, J. Am. Chem. Soc., 116: 8799-8800 (1994); Stemmer et al, Gene, 164: 49-53 (1995); Hoover et al, Nucleic Acids Research, 30: e43 (2002); Xiong et al, Biotechnology Advances, 26: 121-134 (2008); Xiong et al, FEBS Microbiol. Rev., 32: 522-540 (2008); and the like.

Figure 2A:
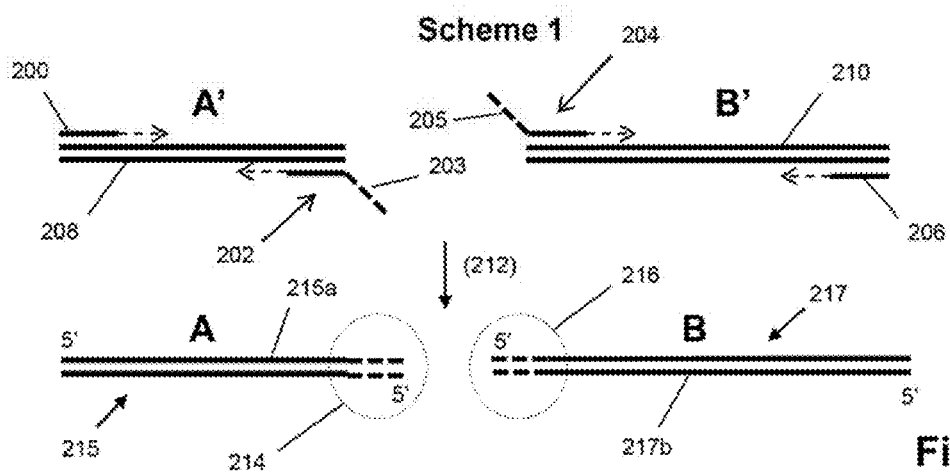
FIGS. 2A-2C illustrate a PCA scheme for linking target sequences where pairs of internal primers have complementary tails.
Figure 2B:
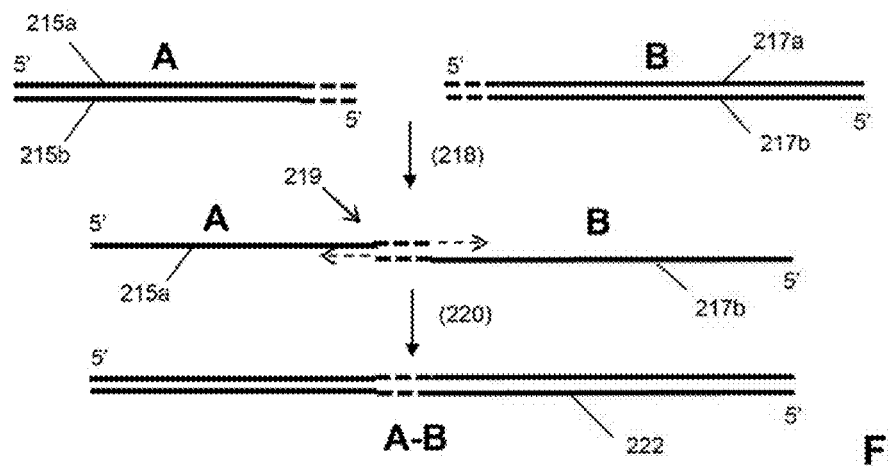
Figure 2C:
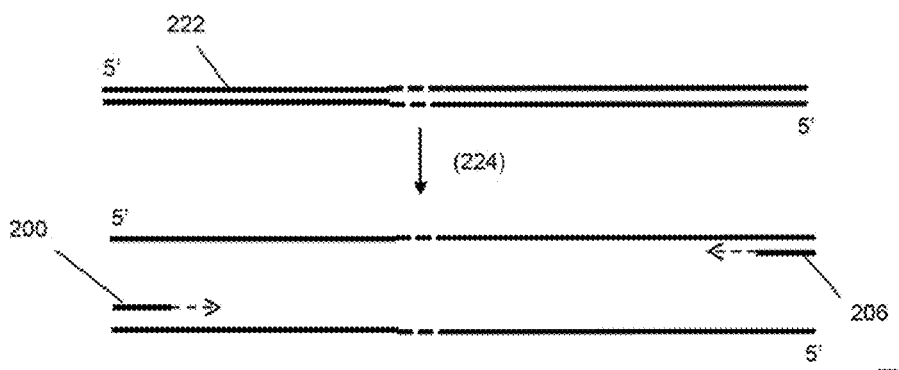

Some PCA formats useful in the present invention are described in FIGS. 2A-2C, 3A-3C, 4A-4C, 5A-5D, and 6A-6E. FIGS. 2A-2C illustrate an exemplary PCA scheme ("Scheme 1") for joining two separate fragments A' (208) and B' (210) into a single fusion product (222). Fragment A' (208) is amplified with primers (200) and (202) and fragment B' (210) is amplified with primers (206) and (204) in the same PCR mixture. Primers (200) and (206) are "outer" primers of the PCA reaction and primers (202) and (204) are the "inner" primers of the PCA reaction. Inner primers (202) and (204) each have a tail (203 and 205, respectively) that are not complementary to A' or B' (or adjacent sequences if A' and B' are segments imbedded in a longer sequence). Tails (203) and (205) are complementary to one another. Generally, such inner primer tails are selected for selective hybridization to its corresponding inner primer (and not elsewhere); but otherwise such tails may vary widely in length and sequence. In one aspect, such tails have a length in the range of from 8 to 30 nucleotides; or a length in the range of from 14 to 24 nucleotides. As the PCRs progress (212), product fragments A (215) and B (217) are produced that incorporate tails (203) and (205) into end regions (214) and (216), respectively. During the PCRs product fragments A (215) and B (217) will denature and some of the "upper" strands (215a) of A anneal (218) to lower strands (217b) of B and the 3' ends are extended (219) to form (220) fusion product A-B (222). Fusion product A-B (222) may be further amplified by an excess of outer primers (200) and (206). In some embodiments, the region of fusion product (222) formed from tails (203) and (205) may include one or more primer binding sites for use in later analysis, such as high-throughput sequencing. Typically, in PDA reactions the concentrations of outer primers are greater than the concentrations of inner primers so that amplification of the fusion product continues after initial formation. For example, in one embodiment for fusing two target nucleic acids outer primer concentration may be from about 10 to 100 times that of the inner primers, e.g. 1 µM for outer primers and 0.01 µM for inner primers. Otherwise, a PCA reaction may comprise the components of a PCR.

Figure 3A:
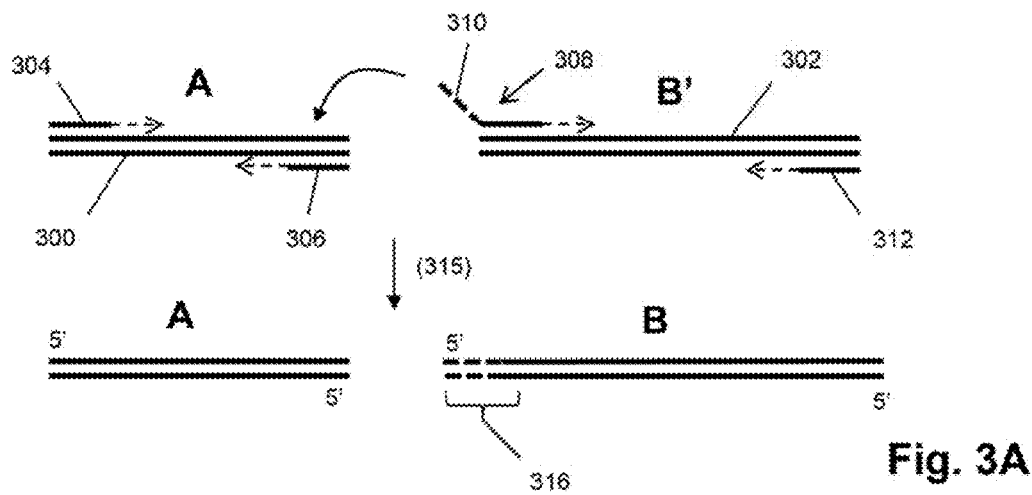
FIGS. 3A-3C illustrate a PCA scheme for linking target sequences where only one primer of each pair of internal primers has a tail that is complementary to an end of a target sequence.
Figure 3B:
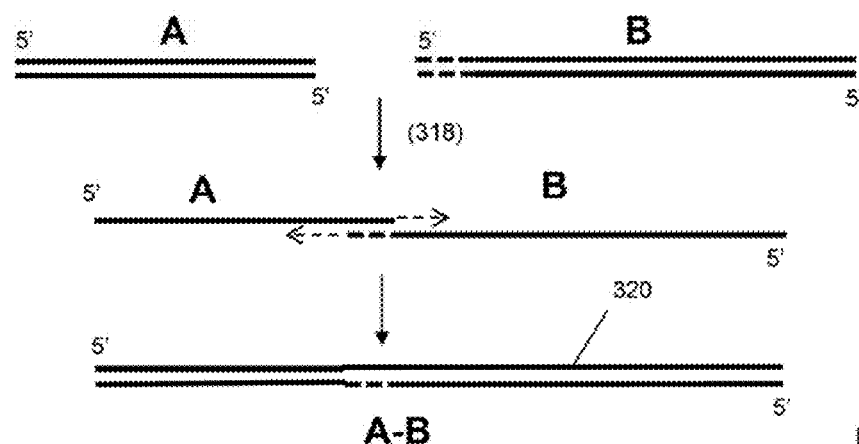
Figure 3C:
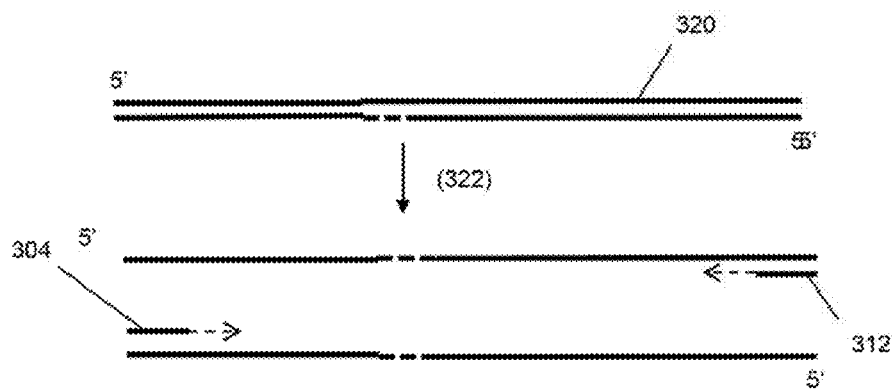

A variation of Scheme 1 is illustrated in FIGS. 3A-3C as Scheme 1(a). As above, fragment A (300) is amplified using primers (304) and (306) and fragment B' (302) is amplified using primers (308) and (312) in PCRs carried out in a common reaction mixture. Outer primers (304) and (312) are employed as above, and inner primer (308) has tail (310); however, instead of tail (310) being complementary to a corresponding tail on primer (306), it is complementary to a segment on the end of fragment A, namely, the same segment that primer (306) is complementary to. The PCRs produce (315) fragments A and B, where B is identical to B' (302) with the addition of segment (316) created by tail (310) of primer (308). As above, as temperature cycling continues (particularly as inner primers become exhausted), the upper fragments of fragment A anneal (318) to the lower fragment of fragment B and are extended to produce fusion product A-B (320), which may be further amplified using primers (304) and (312).

Figure 4A:
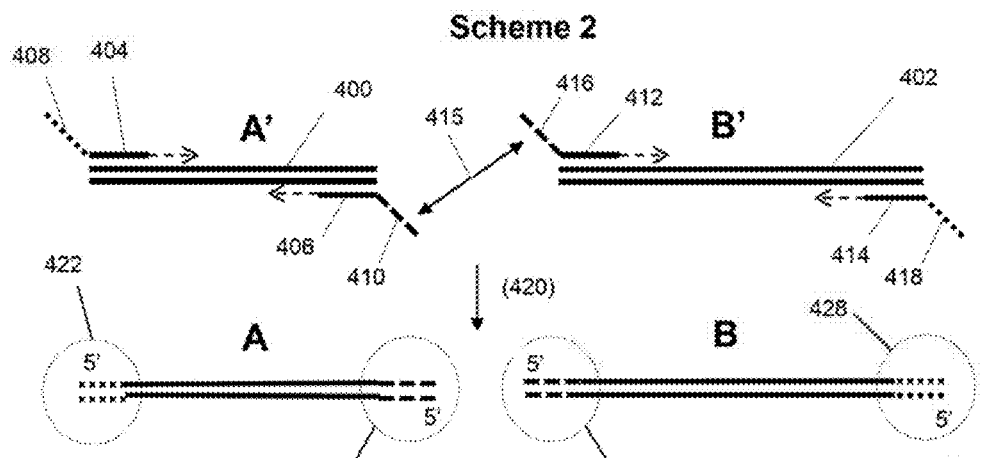
FIGS. 4A-4C illustrate a PCA scheme for linking target sequences where pairs of internal primers have complementary tails and external primers have tails for continued amplification of an assembled product by PCR.
Figure 4B:
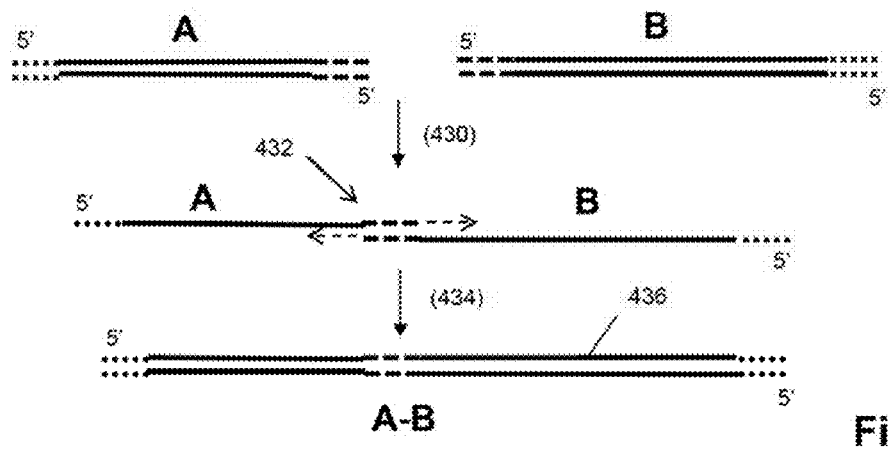
Figure 4C:
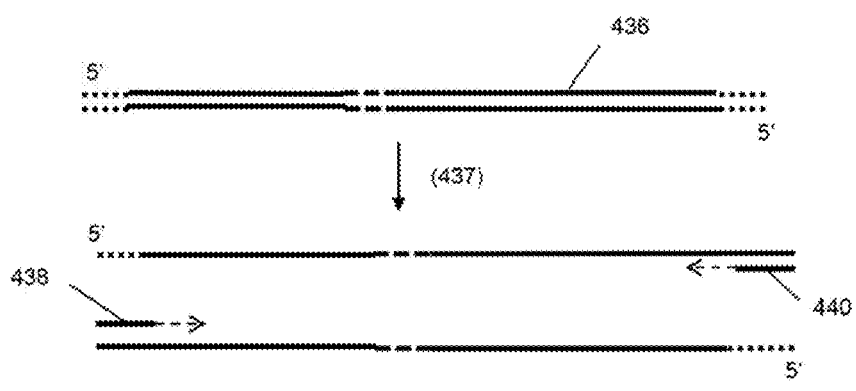

Another embodiment of a PCA that may be used with the invention ("Scheme 2") is illustrated in FIGS. 4A-4C. The embodiment is similar to that of FIGS. 2A-2C, except that outer primers (404) and (414) have tails (408) and (418), respectively, which permit further amplification of a fusion product with predetermined primers. As discussed more fully below, this embodiment is well-suited for multiplexed amplifications. Fragment A' (400) is amplified with primers (404) and (406), having tails (408) and (410), respectively, to produce fragment A, and fragment B' (402) is amplified with primers (412) and (414), having tails (416) and (418), respectively, to produce (420) fragment B. Tails (410 and 416) of inner primers (406 and 412) are selected to complementary (415) to one another. Ends of fragments A and B are augmented by segments (422, 424, 426 and 428) generated by tails (408, 410, 416 and 418, respectively). As with previously described embodiments, upper strands of fragment A anneal (430) to lower strands of fragment B and are extended (432) to form (434) fusion product A-B (436) that may be further amplified (437) using primers (438 and 440) that are the same as primers (404 and 414), but without tails.

As mentioned above, the embodiment of FIGS. 4A-4C, may be used in a multiplex PCA reaction, which is illustrated in FIGS. 5A-5D. There fragments A' (501), B' (502), C' (503), and D' (504) are amplified in PCRs in a common reaction mixture using primer sets (506 and 508) for fragment A', (514 and 516) for fragment B', (522 and 524) for C', and (530 and 532) for D'. All primers have tails: outer primers (506, 516, 522 and 532) each have tails (512, 520, 526 and 536, respectively) that permit both fragment amplification and subsequent fusion product amplification. Sequences of tails (512) and (520) may be the same or different from the sequences of tails (526) and (536), respectively. In one embodiment, the sequences of tails (512, 520, 526 and 536) are the same. Tails of inner primers (518 and 510) are complementary (511) to one another; likewise, tails of inner primers (528 and 534) are complementary (513) to one another. The above PCRs generate fragments A (541), B (542), C (543) and D (544), which further anneal (546) to one another to form complexes (548 and 550) which are extended to form fusion products A-B (552) and C-D (554), respectively.

Figure 5A:
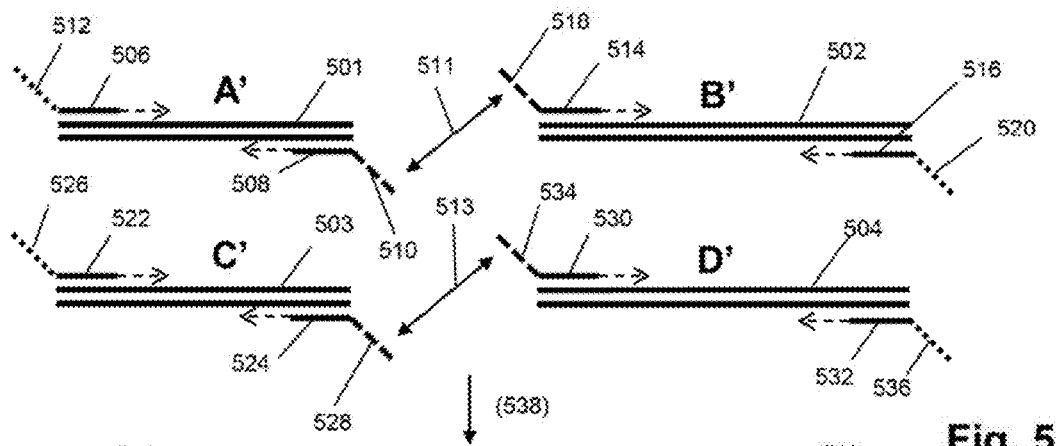
FIGS. 5A-5F illustrate a multiplex of pairwise assemblies of target sequences.
Figure 5B:
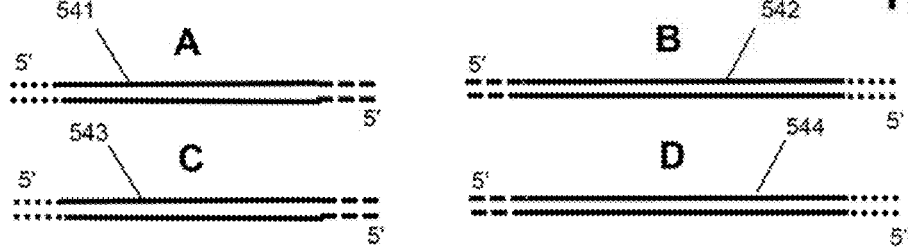
Figure 5C:
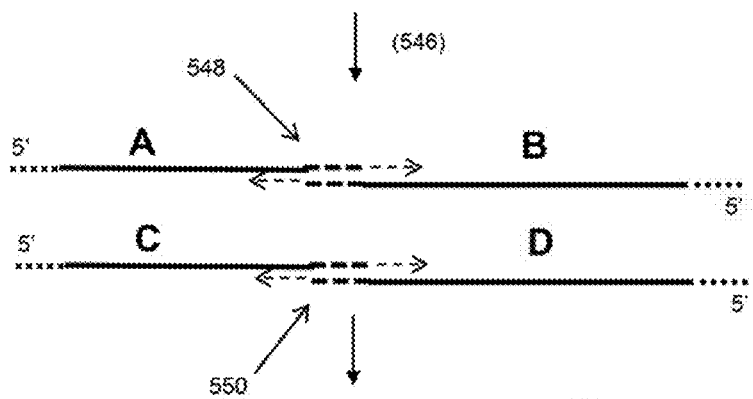
Figure 5D:
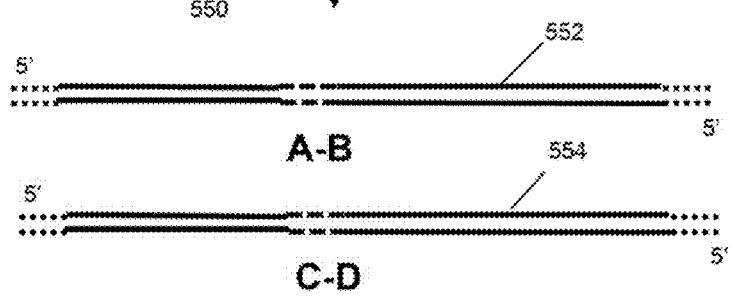
Figure 5E:
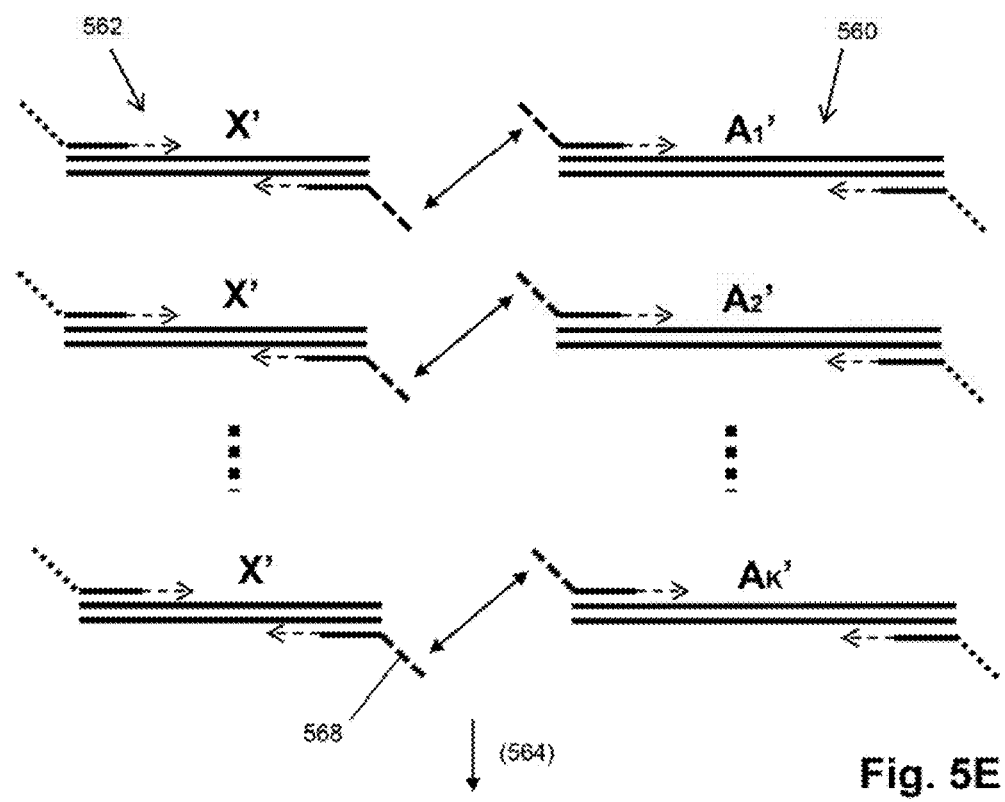
Figure 5F:
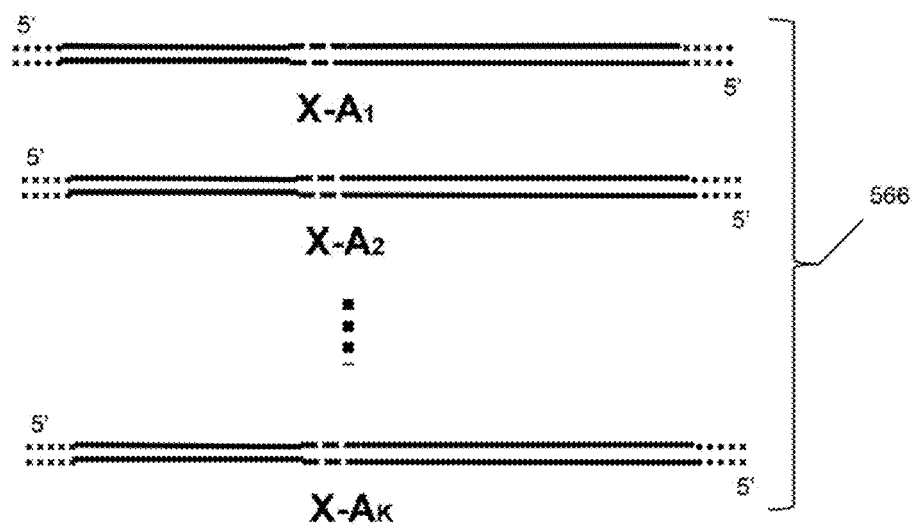

FIGS. 5E and 5F illustrate a generalization of the above embodiment in which multiple different target nucleic acids (560), $A_1', A_2', \ldots A_K'$, are linked to the same target nucleic acid, X' (562) to form (564) multiple fusion products $X-A_1$, $X-A_2, X-A_K$ (566). This embodiment is of particular interest when target nucleic acid, X, is a segment of recombined sequence of a lymphocyte, which can be used as a tag for the lymphocyte that it originates from. In one aspect, X is a clonotype, such as a segment of a V(D)J region of either a B cell or T cell. In one embodiment, a plurality of target nucleic acids, $A_1, A_2, \ldots A_K$, are fused to the clonotype of its cell of origin. In another embodiment, such plurality is between 2 and 1000; and in another embodiment, it is between 2 and 100; and in another embodiment, it is between 2 and 10. In PCA reactions of these embodiments, the concentration of inner primer (568) may be greater than those of inner primers of the various $A_i$ nucleic acids so that there is adequate quantities of the X amplicon to anneal with the many stands of the $A_i$ amplicons. In accordance with a method of the invention, the fusion products (566) are extracted from the reaction mixture (e.g. via conventional double stranded DNA purification techniques, such as available from Qiagen, or the like) and sequenced. The sequences of the outer primers may be selected to permit direct use for cluster formation without further manipulation for sequencing systems such as a Genome Analyzer (Illumina, San Diego, Calif.). In one aspect, X may be a clonotype and $A_1, A_2, \ldots A_K$ may be particular genes or transcripts of interest. After sequencing fusion products, per cell gene expression levels may be tabulated and/or plotted as shown in FIG. 1.

In addition to multiplexed PCA reactions in a parallel sense to simultaneously generate multiple binary fusion products, as illustrated in FIGS. 6A-6E, PCA reactions may be multiplexed in a serial sense to assemble multi-subunit fusion products. As shown in FIG. 6A, fragments A' (601), B' (602) and C' (603) are amplified in a common PCR mixture with primer sets (606 and 608) for A', (610 and 612) for B' and (614 and 616) for C'. All primers have tails: (i) tails (620 and 630) of outer primers (606 and 616) are selected for amplification of outer fragments A' and C' and further amplification of three-way fusion product A-B-C (662) shown in FIG. 6E; (ii) tails (622 and 624) of inner primers (608 and 610) are complementary to one another; and (iii) tails (628 and 626) of inner primers (614 and 612) are complementary to one another. The PCRs generate (632) fragments A (641), B (642) and C (643), which in the reaction form (644) complexes (646 and 648) comprising segments LS1 and LS2, respectively, which in turn are extended to form (650) fusion products A-B (652) and B-C (654). These fusion products are denatured and some cross anneal (658) to one another by way of the common B fragment (656) to form a complex which is extended (660) to form fusion product A-B-C (662). Exemplary, PCA reaction conditions for the above reaction may be as follows: 39.4 µL distilled water combined with 10 µL of 10× buffer (100 mM Tris-HCl, pH 8.3, 500 mM KCl, 15 mM MgCl2, and 0.01% gelatin), 2 µL of a 10 mM solution of each of the dNTPs, 0.5 µL of Taq polymerase (5 units/µL), 1 µL of each outer primer (from a 100 µM stock solution) and 10 µL of each inner primer (from a 0.1 µM stock solution).

Single Cell Analysis

As mentioned above, in one aspect of the invention, cells from a population are disposed in reactors each containing a single cell. This may be accomplished by a variety of large-scale single-cell reactor platforms known in the art, e.g. Clarke et al, U.S. patent publication 2010/0255471; Mathies et al, U.S. patent publication 2010/0285975; Edd et al, U.S. patent publication 2010/0021984; Colston et al, U.S. patent publication 2010/0173394; Love et al, International patent publication WO2009/145925; Muraguchi et al, U.S. patent publication 2009/0181859; Novak et al, Angew. Chem. Int. Ed., 50: 390-395 (2011); and the like, which are incorporated herein by reference. In one aspect, cells are disposed in wells of a microwell array where reactions, such as PCA reactions, take place; in another aspect, cells are disposed in micelles of a water-in-oil emulsion, where micelles serve as reactors. Micelle reactors generated by microfluidics devices, e.g. Mathies et al (cited above) or Edd et al (cited above), are of particular interest because uniform-sized micelles may be generated and cells encounter lower shear and stress than in bulk emulsification processes.

Cells of a sample may be suspended in a PCA reaction mixture prior to disposition into reactors. In one aspect, a PCA reaction mixture is substantially the same as a PCR reaction mixture with inner at least one pair of inner primers and at least one pair of outer primers. Optionally, a PCA reaction mixture may comprise a lysing agent to facilitate access of the PCA reagents to target nucleic acids of isolated cells. Lysing conditions of a PCA reaction may vary widely and may be based on the action of heat, detergent, protease, alkaline, or combinations of such factors. The following references provide guidance for selection of single-cell lysing conditions where a polymerase-based amplification, such as PCA, is employed: Thronhill et al, Prenatal Diagnosis, 21: 490-497 (2001); Kim et al, Fertility and Sterility, 92: 814-818 (2009); and the like. Exemplary lysis conditions for use with PCA reactions are as follows: 1) cells in $H_2O$ at 96° C. for 15 min, followed by 15 min at 10° C.; 2) 200 mM KOH, 50 mM dithiotheitol, heat to 65° C. for 10 min; 3) for 4 μL protease-based lysis buffer: 1 μL of 17 μM SDS combined with 3 μL of 125 μg/mL proteinase K, followed by incubation at 37° C. for 60 min, then 95° C. for 15 min (to inactivate the proteinase K); 4) for 10 μL of a detergent-based lysis buffer: 2 μL $H_2O$, 2 μL 250 ng/μL polyA, 2 μL 10 mM EDTA, 2 μL 250 mM dithiothreitol, 2 μL 0.5% N-laurylsarcosin salt solution. Single-cell analysis platforms, incubation times, lysis buffer and/or PCA reaction other components, their concentrations, reactions volumes and the like, are design choices that are optimized for particular applications by one of ordinary skill in the art.

Nucleic Acid Sequencing Techniques

Any high-throughput technique for sequencing nucleic acids can be used in the method of the invention. DNA sequencing techniques include dideoxy sequencing reactions (Sanger method) using labeled terminators or primers and gel separation in slab or capillary, sequencing by synthesis using reversibly terminated labeled nucleotides, pyrosequencing, 454 sequencing, sequencing by synthesis using allele specific hybridization to a library of labeled clones that is followed by ligation, real time monitoring of the incorporation of labeled nucleotides during a polymerization step, polony sequencing, SOLID sequencing, and the like. These sequencing approaches can thus be used to sequence fusion products of target nucleic acids of interest and clonotypes based on T-cell receptors (TCRs) and/or B-cell receptors (BCRs). In one aspect of the invention, high-throughput methods of sequencing are employed that comprise a step of spatially isolating individual molecules on a solid surface where they are sequenced in parallel. Such solid surfaces may include nonporous surfaces (such as in Solexa sequencing, e.g. Bentley et al, Nature, 456: 53-59 (2008) or Complete Genomics sequencing, e.g. Drmanac et al, Science, 327: 78-81 (2010)), arrays of wells, which may include bead- or particle-bound templates (such as with 454, e.g. Margulies et al, Nature, 437: 376-380 (2005) or Ion Torrent sequencing, U.S. patent publication 2010/0137143 or 2010/0304982), micromachined membranes (such as with SMRT sequencing, e.g. Eid et al, Science, 323: 133-138 (2009)), or bead arrays (as with SOLiD sequencing or polony sequencing, e.g. Kim et al, Science, 316: 1481-1414 (2007)). In another aspect, such methods comprise amplifying the isolated molecules either before or after they are spatially isolated on a solid surface. Prior amplification may comprise emulsion-based amplification, such as emulsion PCR, or rolling circle amplification. Of particular interest is Solexa-based sequencing where individual template molecules are spatially isolated on a solid surface, after which they are amplified in parallel by bridge PCR to form separate clonal populations, or clusters, and then sequenced, as described in Bentley et al (cited above) and in manufacturer's instructions (e.g. TruSeq™ Sample Preparation Kit and Data Sheet, Illumina, Inc., San Diego, Calif., 2010); and further in the following references: U.S. Pat. Nos. 6,090,592; 6,300,070; 7,115,400; and EP0972081B1; which are incorporated by reference. In one embodiment, individual molecules disposed and amplified on a solid surface form clusters in a density of at least $10^5$ clusters per $cm^2$; or in a density of at least $5 \times 10^5$ per $cm^2$; or in a density of at least $10^6$ clusters per $cm^2$. In one embodiment, sequencing chemistries are employed having relatively high error rates. In such embodiments, the average quality scores produced by such chemistries are monotonically declining functions of sequence read lengths. In one embodiment, such decline corresponds to 0.5 percent of sequence reads have at least one error in positions 1-75; 1 percent of sequence reads have at least one error in positions 76-100; and 2 percent of sequence reads have at least one error in positions 101-125.

In one aspect of the invention, multiplex PCR is used to amplify members of a mixture of nucleic acids, particularly mixtures comprising recombined immune molecules such as T cell receptors, B cell receptors, or portions thereof. Guidance for carrying out multiplex PCRs of such immune molecules is found in the following references, which are incorporated by reference: Morley, U.S. Pat. No. 5,296,351; Gorski, U.S. Pat. No. 5,837,447; Dau, U.S. Pat. No. 6,087,096; Von Dongen et al, U.S. patent publication 2006/0234234; European patent publication EP 1544308B1; Faham et al, U.S. patent publication 2010/0151471; Han, U.S. patent publication 2010/0021896; Robins et al, U.S. patent publication 2010/033057; and the like. Such amplification techniques are readily modified by those of ordinary skill in the art to supply outer primers and linking primers of the invention.

Cancer-Related Applications

Detecting cross-lineage rearrangements. Some types of otherwise uncommon rearrangements are common in some cancers and thus can be used to associate them with tumor. For example, cross lineage rearrangements, like T cell receptor (α, β, γ and/or δ) in B cells or B cell receptor (IgH, IgK, and/or IgL) in T cells are common, especially in ALL. The presence of cross lineage rearrangements is likely to support a malignant origin of the clonotype. Demonstrating cross lineage rearrangement can be done by performing linked PCR on a cell by cell basis. Linked PCR amplifies two distinct targets (for example IgH and TCRβ) and create a linked molecule between the two amplified targets. These targets from all the amplified cells can be then pooled and sequenced without losing the information as to whether the two targets are expressed in the same or different cells. In order to get amplification even in the absence of the other rearrangement, another competing product may be used. For example, for B cells, IgH amplification will always occur while the cross lineage TCRβ may or may not occur. Two competing set of primers can be used for the amplification of TCRβ: one that amplifies the rearranged sequences and the other the germ line sequences. Optionally, the two competing sets can be used at different concentrations allowing the rearranged sequence to compete more efficiently when present in the cell. All the cells would have their IgH and TCRβ products amplified and linked, and sequencing would be used to identify those cells with cross lineage rearrangement. Methods for achieving linked PCR are disclosed above. One method to detect cells that do not have functional sequences uses the linked PCR technique mentioned above. In this case, the linking has to occur for the two alleles of the same target. For this purpose, 3 stage PCR can be performed. The first PCR of an immune cell genomic rearrangement is done from one cell with a set of primers (primer A and B) that allow the rearrangement of both alleles to be amplified. Primers A and B are then removed (e.g. by dilution) and a portion of these PCR products can be reamplified with a second set of primers (C and D) which also allow the same product to be amplified. Primers C and B can additionally be designed to include a sequence homology at their 5' termini that allows these 2 PCR products (from A/B and from C/D) to anneal to each other and extend to produce a linked product. After removing primers from this reaction, the two PCR products can be mixed and reamplified by PCR using primers A and D. The result is a linking of the two products, and in 50% of molecules they will carry both alleles. Sequencing would identify high frequency linked non-functional sequences. Specific high frequency non-functional sequences that are consistently linked to a second non-functional sequence are indicative of the potential cancer cell In addition to serving as a marker of cells that have become cancerous IgH is often one of the two pathological translocation partners in lymphoid neoplasms. One example is the t(11:14) that puts the J segment of IgH in close proximity to the cycline D 1 (CCND1) gene resulting in its overexpression. This rearrangement which is referred to as BCL1-IgH occurs in as many as 60-70% of mantle cell lymphoma as well as other lymphoid neoplasms (e.g, 20% of multiple myeloma). Another example is t(14:18) that puts the J segment of IgH in close proximity to BCL2 resulting in its over expression. This rearrangement occurs in up to 90% of follicular lymphoma and 20% of large B cell lymphoma. These rearrangements are typically identified by cytogenetics, Southern blotting, or FISH. PCR has the potential to identify rearrangement at very high sensitivity and specificity as shown by BCR-ABL for the detection of Philadelphia chromosome. Different PCR techniques have been used to the assessment of translocations relevant to lymphoma, with the recently introduced real time PCR (e.g, for BCL2-IgH) being probably the most advanced. There are a few features of BCL1-IgH and BCL2-IgH that make their detection less sensitive and specific than that of BCR-ABL. First, in contrast to BCR-ABL, BCL1-IgH and BCL2-IgH do not generate a fusion protein, and there is no splicing event that generates predictable molecular structure. Instead the breakpoints may span a large region. There are common breakpoints that allow the detection of up to 88% of BCL2-IgH using a combination of primers and ~40% of the BCL1-IgH. This results in missing some patients that have the translocation. Second, these rearrangements may be present in normal individuals that would never get cancer. For example, BLC2-IgH translocation has been found at the level of ~$10^{-5}$ in a large fraction of the normal individuals with over ~4% carrying BCL2-IgH at a frequency of >1/25K. The frequency of BCL2-IgH gets higher with increasing age. It is also hypothesized that different people may have distinct levels of "background" translocation. Presumably the presence of this translocation in normal sample is due to the fact that tumorgenesis is a multi-step process and the BCL2-IgH is not sufficient for tumors to emerge. The presence of this low level background puts a limit on the sensitivity of detection.

Amplification of with a pool of the J primers complementary to all the J segments and primers complementary to the regions upstream of the BCL1 or BCL2 translocation breakpoints can be sequenced. This can generate a method for sensitive detection of these translocations and the cancer cells they appear in. First, deep sequencing of individual isolated molecules (e.g, 100K or 1 million reads) can allow the detection of the appropriate sequences from a small number of cells in a background of amplifications of other loci. In addition, the problem of the background translocations in normal individuals may ameliorate the problem that real time PCR suffer from. There is evidence that, at least in some cases, the background translocations are not clonal but rather appear repeatedly in the same patient. Using sequencing one can distinguish the different translocation events to obtain frequency of the independent translocation events. Since the breakpoint of different translocations is likely to be distinct translocation events can be distinguished from each other. Alternatively or additionally, a linking PCR using the translocation with a B or T cell receptor gene can be done to provide a unique barcode for the translocation. The linking can also be done statistically using a set of dilution samples as described above.

Similarly additional data relating to the status of the cell containing the cancer-related clonotype can be used to predict likelihood of recurrence. For example, the presence of certain markers (surface or non-surface) can be an indication of the functional status of the cell and hence the likelihood of recurrence. Sequencing before and after the capture of cells with the relevant markers can determine the fraction of cells with the cancer clonotype that carry the relevant markers. Similarly some markers relevant to the likelihood of recurrence (e.g., expression of some gene relating to cell growth) can be assessed at the RNA level. This can be done by several methods including linking PCR as described above. Finally, it is possible that the level of immune receptor specific RNA in the tumor cell can have functional consequence and association with the likelihood of recurrence. This level can be assessed by doing linking PCR between a control gene 1 that can link to either the immune receptor rearrangement or control gene 2. The relative fraction of the two products can be indicative of the relative amount of the RNA in the cell. Another method involves comparing the RNA level to the DNA level of the immune receptor rearrangement. The frequency of the cancer-specific clonotype in the DNA identifies the relative level of the cancer-specific clonotype. The frequency of the same clonotype can then be assessed from RNA, and the relative frequency in RNA and in DNA can be followed. A change in this relative frequency can be indicative of a change in the likelihood of recurrence.

While the present invention has been described with reference to several particular example embodiments, those skilled in the art will recognize that many changes may be made thereto without departing from the spirit and scope of the present invention. The present invention is applicable to a variety of sensor implementations and other subject matter, in addition to those discussed above.

Defintions

Unless otherwise specifically defined herein, terms and symbols of nucleic acid chemistry, biochemistry, genetics, and molecular biology used herein follow those of standard treatises and texts in the field, e.g. Kornberg and Baker, DNA Replication, Second Edition (W.H. Freeman, New York, 1992); Lehninger, Biochemistry, Second Edition (Worth Publishers, New York, 1975); Strachan and Read, Human Molecular Genetics, Second Edition (Wiley-Liss, New York, 1999); Abbas et al, Cellular and Molecular Immunology, 6$^{th}$ edition (Saunders, 2007).

"Amplicon" means the product of a polynucleotide amplification reaction; that is, a clonal population of polynucleotides, which may be single stranded or double stranded, which are replicated from one or more starting sequences. The one or more starting sequences may be one or more copies of the same sequence, or they may be a mixture of different sequences. Preferably, amplicons are formed by the amplification of a single starting sequence. Amplicons may be produced by a variety of amplification reactions whose products comprise replicates of the one or more starting, or target, nucleic acids. In one aspect, amplification reactions producing amplicons are "template-driven" in that base pairing of reactants, either nucleotides or oligonucleotides, have complements in a template polynucleotide that are required for the creation of reaction products. In one aspect, template-driven reactions are primer extensions with a nucleic acid polymerase or oligonucleotide ligations with a nucleic acid ligase. Such reactions include, but are not limited to, polymerase chain reactions (PCRs), linear polymerase reactions, nucleic acid sequence-based amplification (NASBAs), rolling circle amplifications, and the like, disclosed in the following references that are incorporated herein by reference: Mullis et al, U.S. Pat. Nos. 4,683,195; 4,965,188; 4,683,202; 4,800,159 (PCR); Gelfand et al, U.S. Pat. No. 5,210,015 (real-time PCR with "taqman" probes); Wittwer et al, U.S. Pat. No. 6,174,670; Kacian et al, U.S. Pat. No. 5,399,491 ("NASBA"); Lizardi, U.S. Pat. No. 5,854,033; Aono et al, Japanese patent publ. JP 4-262799 (rolling circle amplification); and the like. In one aspect, amplicons of the invention are produced by PCRs. An amplification reaction may be a "real-time" amplification if a detection chemistry is available that permits a reaction product to be measured as the amplification reaction progresses, e.g. "real-time PCR" described below, or "real-time NASBA" as described in Leone et al, Nucleic Acids Research, 26: 2150-2155 (1998), and like references. As used herein, the term "amplifying" means performing an amplification reaction. A "reaction mixture" means a solution containing all the necessary reactants for performing a reaction, which may include, but be not limited to, buffering agents to maintain pH at a selected level during a reaction, salts, co-factors, scavengers, and the like.

"Clonotype" means a recombined nucleotide sequence of a T cell or B cell encoding a T cell receptor (TCR) or B cell receptor (BCR), or a portion thereof. In one aspect, a collection of all the distinct clonotypes of a population of lymphocytes of an individual is a repertoire of such population, e.g. Arstila et al, Science, 286: 958-961 (1999); Yassai et al, Immunogenetics, 61: 493-502 (2009); Kedzierska et al, Mol. Immunol., 45(3): 607-618 (2008); and the like. A "clonotype profile," or "repertoire profile," is a tabulation or representation of clonotypes of a population of T cells and/or B cells (such as a peripheral blood sample containing such cells) that includes substantially all of the repertoire's clonotypes and their relative abundances. As used herein, "clonotype profile," "repertoire profile," and "repertoire" are used interchangeably. (That is, the term "repertoire," as discussed more fully below, means a repertoire measured from a sample of lymphocytes). In one aspect of the invention, clonotypes comprise portions of an immunoglobulin heavy chain (IgH) or a TCR β chain. In other aspects of the invention, clonotypes may be based on other recombined molecules, such as immunoglobulin light chains or TCRα chains, or portions thereof.

"Complementarity determining regions" (CDRs) mean regions of an immunoglobulin (i.e., antibody) or T cell receptor where the molecule complements an antigen's conformation, thereby determining the molecule's specificity and contact with a specific antigen. T cell receptors and immunoglobulins each have three CDRs: CDR1 and CDR2 are found in the variable (V) domain, and CDR3 includes some of V, all of diverse (D) (heavy chains only) and joint (J), and some of the constant (C) domains.

"Kit" refers to any delivery system for delivering materials or reagents for carrying out a method of the invention. In the context of reaction assays, such delivery systems include systems that allow for the storage, transport, or delivery of reaction reagents (e.g., primers, enzymes, etc. in the appropriate containers) and/or supporting materials (e.g., buffers, written instructions for performing the assay etc.) from one location to another. For example, kits include one or more enclosures (e.g., boxes) containing the relevant reaction reagents and/or supporting materials. Such contents may be delivered to the intended recipient together or separately. For example, a first container may contain an enzyme for use in an assay, while a second container contains primers.

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for ease of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 µm to about 0.1 µm. Microfluidics devices typically have volume capacities in the range of from 1 µL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858, 195; 6,010,607; and 6,033,546; Soane et al, U.S. Pat. Nos. 5,126,022 and 6,054,034; Nelson et al, U.S. Pat. No. 6,613, 525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437.

"Polymerase chain reaction," or "PCR," means a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g. exemplified by the references: McPherson et al, editors, PCR: A Practical Approach and PCR2: A Practical Approach (IRL Press, Oxford, 1991 and 1995, respectively). For example, in a conventional PCR using Taq DNA polymerase, a double stranded target nucleic acid may be denatured at a temperature>90° C., primers annealed at a temperature in the range 50-75° C., and primers extended at a temperature in the range 72-78° C. The term "PCR" encompasses derivative forms of the reaction, including but not limited to, RT-PCR, real-time PCR, nested PCR, quantitative PCR, multiplexed PCR, and the like. PCR reaction volumes typically range from a few hundred nanoliters, e.g. 200 nL, to a few hundred μL, e.g. 200 μL. "Reverse transcription PCR," or "RT-PCR," means a PCR that is preceded by a reverse transcription reaction that converts a target RNA to a complementary single stranded DNA, which is then amplified, e.g. Tecott et al, U.S. Pat. No. 5,168,038, which patent is incorporated herein by reference. "Real-time PCR" means a PCR for which the amount of reaction product, i.e. amplicon, is monitored as the reaction proceeds. There are many forms of real-time PCR that differ mainly in the detection chemistries used for monitoring the reaction product, e.g. Gelfand et al, U.S. Pat. No. 5,210,015 ("taqman"); Wittwer et al, U.S. Pat. Nos. 6,174,670 and 6,569,627 (intercalating dyes); Tyagi et al, U.S. Pat. No. 5,925,517 (molecular beacons); which patents are incorporated herein by reference. Detection chemistries for real-time PCR are reviewed in Mackay et al, Nucleic Acids Research, 30: 1292-1305 (2002), which is also incorporated herein by reference. "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al, Anal. Biochem., 273: 221-228 (1999) (two-color real-time PCR). Usually, distinct sets of primers are employed for each sequence being amplified. "Quantitative PCR" means a PCR designed to measure the abundance of one or more specific target sequences in a sample or specimen. Quantitative PCR includes both absolute quantitation and relative quantitation of such target sequences. Quantitative measurements are made using one or more reference sequences that may be assayed separately or together with a target sequence. The reference sequence may be endogenous or exogenous to a sample or specimen, and in the latter case, may comprise one or more competitor templates. Typical endogenous reference sequences include segments of transcripts of the following genes: β-actin, GAPDH, $β_2$-microglobulin, ribosomal RNA, and the like. Techniques for quantitative PCR are well-known to those of ordinary skill in the art, as exemplified in the following references that are incorporated by reference: Freeman et al, Biotechniques, 26: 112-126 (1999); Becker-Andre et al, Nucleic Acids Research, 17: 9437-9447 (1989); Zimmerman et al, Biotechniques, 21: 268-279 (1996); Diviacco et al, Gene, 122: 3013-3020 (1992); Becker-Andre et al, Nucleic Acids Research, 17: 9437-9446 (1989); and the like.

"Polymerase cycling assembly" or "PCA" reaction (also referred to herein as "linked PCR") means a PCR that comprises at least one pair of outer primers and at least one pair of inner primers. An inner primer has a 3' portion that is complementary to a target nucleic acid (or its complement) and a 5' portion that is complementary to the 5' portion of another inner primer corresponding to a different target nucleic acid.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, $2^{nd}$ Edition (Cold Spring Harbor Press, New York, 2003).

"Repertoire" means a set of distinct recombined nucleotide sequences that encode T cell receptors (TCRs) or B cell receptors (BCRs), or fragments thereof, respectively, in a population of lymphocytes of an individual, wherein the nucleotide sequences of the set have a one-to-one correspondence with distinct lymphocytes or their clonal subpopulations for substantially all of the lymphocytes of the population. Member nucleotide sequences of a repertoire are referred to herein as a "clonotype." In one aspect, a repertoire comprises any segment of nucleic acid common to a T cell or a B cell population which has undergone somatic recombination during the development of TCRs or BCRs, including normal or aberrant (e.g. associated with cancers) precursors thereof, including, but not limited to, any of the following: an immunoglobulin heavy chain (IgH) or subsets thereof (e.g. an IgH variable region, CDR3 region, or the like), an immunoglobulin light chain or subsets thereof (e.g. a variable region, CDR region, or the like), T cell receptor α chain or subsets thereof, T cell receptor β chain or subsets thereof (e.g. variable region, CDR3, V(D)J region, or the like), a CDR (including CDR1, CDR2 or CDR3, of either TCRs or BCRs, or combinations of such CDRs), V(D)J regions of either TCRs or BCRs, hypermutated regions of IgH variable regions, or the like. In one aspect, a repertoire is selected so that its diversity (i.e. the number of distinct nucleic acid sequences in the set) is large enough so that substantially every T cell or B cell or clone thereof in an individual carries a unique nucleic acid sequence of such repertoire. That is, in accordance with the invention, a practitioner may select for defining clonotypes a particular segment or region of recombined nucleic acids that encode TCRs or BCRs that do not reflect the full diversity of a population of T cells or B cells; however, preferably, clonotypes are defined so that they do reflect the diversity of the population of T cells and/or B cells from which they are derived. That is, preferably each different clone of a sample has different clonotype. In other aspects of the invention, the population of lymphocytes corresponding to a repertoire may be circulating B cells, or may be circulating T cells, or may be subpopulations of either of the foregoing populations, including but not limited to, CD4+ T cells, or CD8+ T cells, or other subpopulations defined by cell surface markers, or the like. In one embodiment, a repertoire of human TCR β chains comprises a number of distinct nucleotide sequences in the range of from $0.3 \times 10^6$ to $1.8 \times 10^6$, or in the range of from $0.5 \times 10^6$ to $1.5 \times 10^6$, or in the range of from $0.8 \times 10^6$ to $1.2 \times 10^6$. Such subpopulations may be acquired by taking samples from particular tissues, e.g. bone marrow, or lymph nodes, or the like, or by sorting or enriching cells from a sample (such as peripheral blood) based on one or more cell surface markers, size, morphology, or the like. In still other aspects, the population of lymphocytes corresponding to a repertoire may be derived from disease tissues, such as a tumor tissue, an infected tissue, or the like. In a particular embodiment, a repertoire of the invention comprises a set of nucleotide sequences encoding substantially all segments of the V(D)J region of an IgH chain. In one aspect, "substantially all" as used herein means every segment having a relative abundance of 0.001 percent or higher; or in another aspect, a relative abundance of 0.0001 percent or higher. In another particular embodiment, a repertoire of the invention comprises a set of nucleotide sequences that encodes substantially all segments of the V(D)J region of a TCR β chain. In another embodiment, a repertoire of the invention comprises a set of nucleotide sequences having lengths in the range of from 25-200 nucleotides and including segments of the V, D, and J regions of a TCR β chain. In another embodiment, a repertoire of the invention comprises a set of nucleotide sequences having lengths in the range of from 25-200 nucleotides and including segments of the V, D, and J regions of an IgH chain. In another embodiment, a repertoire of the invention comprises a number of distinct nucleotide sequences that is substantially equivalent to the number of lymphocytes expressing a distinct IgH chain. In another embodiment, a repertoire of the invention comprises a number of distinct nucleotide sequences that is substantially equivalent to the number of lymphocytes expressing a distinct TCR β chain. In still another embodiment, "substantially equivalent" means that with ninety-nine percent probability a repertoire of nucleotide sequences will include a nucleotide sequence encoding an IgH or TCR β or portion thereof carried or expressed by every lymphocyte of a population of an individual at a frequency of 0.001 percent or greater. In still another embodiment, "substantially equivalent" means that with ninety-nine percent probability a repertoire of nucleotide sequences will include a nucleotide sequence encoding an IgH or TCR β or portion thereof carried or expressed by every lymphocyte present at a frequency of 0.0001 percent or greater. The foregoing sets of clonotypes are sometimes referred to herein as representing the "full repertoire" of IgH and/or TCRβ sequences.

What is claimed is:

1. A method of distinguishing by single cell analysis multiple subpopulations of a population of lymphocytes, the method comprising the steps of;
    providing multiple reactors each containing a single lymphocyte of the population in a polymerase cycling assembly (PCA) reaction mixture comprising a pair of outer primers and one or more pairs of linking primers, at least one pair of such outer and linking primers being specific for a nucleic acid containing a clonotype and one or more pairs of such outer and linking primers being specific for a plurality of target nucleic acids which is characteristic of a subpopulation of lymphocytes, wherein the clonotype is a recombined nucleic acid sequence of a B cell encoding a B cell receptor or portion thereof, and/or a T cell encoding a T cell receptor or portion thereof, respectively;
    performing a PCA reaction in each reactor to form a plurality of different kinds of fusion products comprising a plurality of different target nucleic acids and a clonotype of the single lymphocyte therein;
    sequencing the fusion products from the reactors; and
    classifying each single lymphocyte into a subpopulation by the target nucleic acids associated with its clonotype.

2. The method. of claim 1 wherein said multiple reactors are aqueous micelles of a water-in-oil emulsion.

3. The method of claim 2 wherein said water-in-oil emulsion is generated by a microfluidics device.

4. The method of claim 1 wherein said nucleic acid containing said clonotype and said one or more target nucleic acids are RNA and wherein said step of classifying includes determining the relative expression levels of said plurality of target nucleic acids.

5. The method of claim 1 further comprising a step of lysing said single lymphocytes in said reactors prior to said step of performing a PCA reaction.

6. The method of claim 1 wherein said clonotype comprises a portion of an immunoglobulin heavy chain (IgH) or a TCR β chain.

* * * * *

UNITED STATES PATENT AND TRADEMARK OFFICE
CERTIFICATE OF CORRECTION

| | |
|---|---|
| PATENT NO. | : 8,507,205 B2 |
| APPLICATION NO. | : 13/100395 |
| DATED | : August 13, 2013 |
| INVENTOR(S) | : Malek Faham et al. |

It is certified that error appears in the above-identified patent and that said Letters Patent is hereby corrected as shown below:

In the Claims:

COLUMN 16, LINE 11:

"the steps of;" should read --the steps of:--

COLUMN 16, LINE 32:

"The method. of claim 1" should read --The method of claim 1--

Signed and Sealed this
Twelfth Day of November, 2013

Teresa Stanek Rea
*Deputy Director of the United States Patent and Trademark Office*